(12) United States Patent
An et al.

(10) Patent No.: US 9,365,900 B2
(45) Date of Patent: Jun. 14, 2016

(54) DIAGNOSIS KIT AND CHIP FOR BLADDER CANCER USING BLADDER CANCER SPECIFIC METHYLATION MARKER GENE

(71) Applicant: GENOMICTREE, INC., Daejeon (KR)

(72) Inventors: Sung Whan An, Daejeon (KR); Young Ho Moon, Daejeon (KR); Tae Jeong Oh, Daejeon (KR)

(73) Assignee: GENOMICTREE, INC., Daejeon (KR)

( * ) Notice: Subject to any disclaimer, the term of this patent is extended or adjusted under 35 U.S.C. 154(b) by 0 days.

(21) Appl. No.: 13/627,474

(22) Filed: Sep. 26, 2012

(65) Prior Publication Data
US 2013/0123116 A1 May 16, 2013

Related U.S. Application Data

(62) Division of application No. 12/744,491, filed as application No. PCT/KR2008/007081 on Dec. 1, 2008, now abandoned.

(30) Foreign Application Priority Data

Nov. 30, 2007 (KR) ........................ 10-2007-0124015

(51) Int. Cl.
*C12Q 1/68* (2006.01)
(52) U.S. Cl.
CPC .............. *C12Q 1/6886* (2013.01); *C12Q 1/686* (2013.01); *C12Q 2600/154* (2013.01); *C12Q 2600/156* (2013.01)
(58) Field of Classification Search
CPC . C12Q 1/686; C12Q 1/6886; C12Q 2600/154
USPC .................................................. 435/6.1, 6.14
See application file for complete search history.

(56) References Cited

U.S. PATENT DOCUMENTS

| | | | |
|---|---|---|---|
| 6,812,339 B1 | 11/2004 | Venter et al. | |
| 7,354,713 B2 | 4/2008 | Mertz et al. | |
| 7,972,772 B2 | 7/2011 | Nakamura | |
| 8,062,892 B2 | 11/2011 | Schlegel | |
| 8,173,602 B2 | 5/2012 | Albertson et al. | |
| 8,513,028 B2 | 8/2013 | Jang | |
| 2002/0137086 A1 | 9/2002 | Olek et al. | |
| 2007/0298506 A1 | 12/2007 | Ordway et al. | |
| 2010/0304992 A1 | 12/2010 | An et al. | |

FOREIGN PATENT DOCUMENTS

| | | |
|---|---|---|
| CA | 2288235 A1 | 3/1998 |
| JP | 2002511749 A | 4/2002 |
| WO | 0119845 A1 | 3/2001 |
| WO | 2007143037 A2 | 12/2007 |

OTHER PUBLICATIONS

Promega's Protocols & Applications Guide, Chapter 1: Nucleic Acid Amplification; 2011, pp. 1-26.
Strachan, et al.; "Human Molecular Genetics," 2nd Edition, Chapter 5, 1999, pp. 1-35.
Liu, Tong, et al.; "Regulation of Cdx2 epression by promoter methylation, and effects of Cdx2 transfection on morphology and gene expression of humanespphageal epithelial cells," Carcinogenesis, 2007, pp. 488-496, vol. 28, No. 2.
Chan, Michael W.T. et al.; "hypermethylation of Multiple Genes in Tumor Tissues and Voided Urine in Urinary Bladder Cancer Patients," Clinical Cancer Research, 2002, pp. 464-470, vol. 8, No. 2.
Suh, Namsoo, et al.; "Value of CDX2, villin, and alpha-methylacyl coenzyme A racemase immunostains in the distinction between primary adenocarcinoma of the bladder and secondary colorectal adenocarcinoma," Modern Pathology, 2005, pp. 1217-1222, vol. 18, No. 9.
Marsit, C.J. et al.; "Examination of CpG Island Methylator Phenotype and Implications of Methylation Profiles in Solid Tumors," Cancer Research, 2006, pp. 10621-10629, vol. 66, No. 21.
Yates D.R. et al.; "Promoter Hypermethylation Identifies Progression Risk in Bladder Cancer," Clinical Cancer Research, 2007, pp. 2046-2053, vol. 13, No. 7.
Utikal, J. et al.; "The expression of metastasis suppressor MIM/MTSS1 is regulated by DNA methylation," International Journal of Cancer, 2006, pp. 2287-2293, vol. 119, No. 10.
Kawamoto, K, et al., "p16INK4a and p14ARF methylation as a potential biomarker for human bladder cancer," Biochemical and Biophysical Research Communications, 2006, pp. 790-796, vol. 339, No. 3.
Esteller, M. et al.; "Detection of Aberrant Promoter Hypermethylation of Tumor Suppressor Genes in Serum DNA from non-Small Cell Lung Cancer Patients," Cancer Research, 1999, pp. 67-70, vol. 59.
Sanchez-Cespedes, M, et al.; "Gene Promoter Hypermethylation in Tumors and Serum of Head and Neck Cancer Patients," Cancer Research, 2000, pp. 892-895, vol. 60.
Ahlquist, D.A. et al.; "Colorectal Cancer Screening by Detection of Altered Human DNA in Stool: Feasibility of a Multitarget Assay Panel," Gastroenterology, 2000, pp. 1219-1227, vol. 119, American Gastroenterological Association.
Fraga, M.F., et al.; "The affinity of different MBD proteins for a specific methylated locus depends on their intrinsic binding properties," Nucleic Acids Research, 2003, pp. 1765-1774, vol. 31, No. 6, Oxford University Press.
Comb, Michael, et al.; "CpG methylation inhibits proenkephalin gene expression and binding of the transcription factor AP-2," Nucleic Acids Research, 1990, pp. 3975-3982, vol. 18, No. 13.

(Continued)

*Primary Examiner* — Antonio Galisteo Gonzalez
(74) *Attorney, Agent, or Firm* — Tristan A. Fuierer; Moore & Van Allen, PLLC

(57) ABSTRACT

The present invention relates to a kit and nucleic acid chip for diagnosing bladder cancer using a bladder cancer-specific marker gene. More particularly, the invention relates to a kit and nucleic acid chip for diagnosing bladder cancer, which can detect the promoter methylation of a bladder cancer-specific gene, the promoter or exon region of which is methylated specifically in transformed cells of bladder cancer. The use of the diagnostic kit or nucleic acid chip of the invention enables diagnosis of bladder cancer at an early stage of transformation, thus enabling early diagnosis of bladder cancer, and can diagnose bladder cancer in a more accurate and rapid manner compared to a conventional method.

7 Claims, 17 Drawing Sheets

(56) References Cited

OTHER PUBLICATIONS

Ho, Shuk-Mei, et al.; "Techniques used in studies of epigenome dysregulation due to aberrant DNA methylation: An emphasis on fetal-based adult diseases," Reproductive Toxicology, 2007, pp. 267-282, vol. 23.

Old, Dr. Robert W., et al.; Candidate epigentic biomarkers for non-invasice prenatal diagnosis of Down syndrome, Reproductive Biomedicine Online, 2007, pp. 227-235, vol. 15, No. 2.

Tanay, Amos, et al.; "Hyperconserved CpG domains underlie Polycomb-binding sites," PNAS, 2007, pp. 5521-5526, vol. 104.

Chinese Office Action, May 16, 2013.

Das et al., DNA Methylation and Cancer, Journal of Clinical Oncology, Nov. 15, 2004, vol. 22, pp. 4632-4641.

Costello et al., Aberrant CpG-island methylation has non-random and tumour-type-specific patterns, Nature Genetics, Feb. 2000, vol. 25, pp. 132-138.

Fukushima, et al.; "Aberrant methylation of preproenkephalin and p16 genes in pancreatic intraepithelial neoplasia and pancreatic ductal adenocarcinoma," American Journal of Pathology, May 2002, pp. 1573-1581, vol. 160.

Uekt, et al.; "Identification and characterization of differentiall menthylated CpG islands in pancreatic carcinoma," Cancer Research, Dec. 2001, pp. 8540-8546, vol. 61.

Goo, et al.; "Stromal mesenchyme cell genes of the human prostate and bladder," BMC Urology, Dec. 2005, pp. 1-11, vol. 5.

Schulz, W.A.; "DNA methylation in urological malignancies (review)," International Journal of Oncology, Jul. 1998, pp. 151-167, vol. 13.

Yamaki, et al.; "Molecular mechanisms of human single minded2 (SIM2) gene expression: identification of a promrter site in the SIM2 genomic sequence," Gene, May 2001, pp. 265-275, vol. 270.

Japanese Office Action, Jun. 5, 2014.

SEQUENCE LISTING

```
<160> NUMBER OF SEQ ID NOS: 42

<210> SEQ ID NO 1
<211> LENGTH: 24
<212> TYPE: DNA
<213> ORGANISM: Artificial Sequence
<220> FEATURE:
<223> OTHER INFORMATION: Synthetic Construct

<400> SEQUENCE: 1
tggtgtttgt gttattatta atag                                              24

<210> SEQ ID NO 2
<211> LENGTH: 21
<212> TYPE: DNA
<213> ORGANISM: Artificial Sequence
<220> FEATURE:
<223> OTHER INFORMATION: Synthetic Construct

<400> SEQUENCE: 2
cacctccttc ccactaaact a                                                 21

<210> SEQ ID NO 3
<211> LENGTH: 19
<212> TYPE: DNA
<213> ORGANISM: Artificial Sequence
```

```
<220> FEATURE:
<223> OTHER INFORMATION: Synthetic Construct

<400> SEQUENCE: 3
gtaagggtat gggaattga                                              19

<210> SEQ ID NO 4
<211> LENGTH: 22
<212> TYPE: DNA
<213> ORGANISM: Artificial Sequence
<220> FEATURE:
<223> OTHER INFORMATION: Synthetic Construct

<400> SEQUENCE: 4
cccttaaaaa cctaacaaaa tc                                          22

<210> SEQ ID NO 5
<211> LENGTH: 21
<212> TYPE: DNA
<213> ORGANISM: Artificial Sequence
<220> FEATURE:
<223> OTHER INFORMATION: Synthetic Construct

<400> SEQUENCE: 5
ggagtgggat tgaggagatt t                                           21

<210> SEQ ID NO 6
<211> LENGTH: 19
<212> TYPE: DNA
<213> ORGANISM: Artificial Sequence
<220> FEATURE:
<223> OTHER INFORMATION: Synthetic Construct

<400> SEQUENCE: 6
aaacccaacc aaccctcat                                              19

<210> SEQ ID NO 7
<211> LENGTH: 23
<212> TYPE: DNA
<213> ORGANISM: Artificial Sequence
<220> FEATURE:
<223> OTHER INFORMATION: Synthetic Construct

<400> SEQUENCE: 7
agtaagttta tgggaggggg att                                         23

<210> SEQ ID NO 8
<211> LENGTH: 25
<212> TYPE: DNA
<213> ORGANISM: Artificial Sequence
<220> FEATURE:
<223> OTHER INFORMATION: Synthetic Construct

<400> SEQUENCE: 8
cccccataca acatacttat actca                                       25

<210> SEQ ID NO 9
<211> LENGTH: 26
<212> TYPE: DNA
<213> ORGANISM: Artificial Sequence
<220> FEATURE:
<223> OTHER INFORMATION: Synthetic Construct

<400> SEQUENCE: 9
ggaggaatgt tattgtttaa agagat                                      26
```

```
<210> SEQ ID NO 10
<211> LENGTH: 22
<212> TYPE: DNA
<213> ORGANISM: Artificial Sequence
<220> FEATURE:
<223> OTHER INFORMATION: Synthetic Construct

<400> SEQUENCE: 10 caacccccttc taaaaaatat cc                                              22

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
gggtttggag ttaggttatg                                                  20

<210> SEQ ID NO 12
<211> LENGTH: 22
<212> TYPE: DNA
<213> ORGANISM: Artificial Sequence
<220> FEATURE:
<223> OTHER INFORMATION: Synthetic Construct

<400> SEQUENCE: 12
aaatctaaac ttacccccaa ct                                               22

<210> SEQ ID NO 13
<211> LENGTH: 28
<212> TYPE: DNA
<213> ORGANISM: Artificial Sequence
<220> FEATURE:
<223> OTHER INFORMATION: Synthetic Construct

<400> SEQUENCE: 13
atattttatt gtatgggttt tttaatag                                         28

<210> SEQ ID NO 14
<211> LENGTH: 19
<212> TYPE: DNA
<213> ORGANISM: Artificial Sequence
<220> FEATURE:
<223> OTHER INFORMATION: Synthetic Construct

<400> SEQUENCE: 14
acaacctcaa caaaaaatc                                                   19

<210> SEQ ID NO 15
<211> LENGTH: 19
<212> TYPE: DNA
<213> ORGANISM: Artificial Sequence
<220> FEATURE:
<223> OTHER INFORMATION: Synthetic Construct

<400> SEQUENCE: 15 agataggggga taattttat                                                  19

<210> SEQ ID NO 16
<211> LENGTH: 18
<212> TYPE: DNA
<213> ORGANISM: Artificial Sequence
<220> FEATURE:
<223> OTHER INFORMATION: Synthetic Construct
```

```
<400> SEQUENCE: 16
cctcccaaac taaaattt                                                      18

<210> SEQ ID NO 17
<211> LENGTH: 23
<212> TYPE: DNA
<213> ORGANISM: Artificial Sequence
<220> FEATURE:
<223> OTHER INFORMATION: Synthetic Construct

<400> SEQUENCE: 17
gtagaaggga ataaggttg aaa                                                 23

<210> SEQ ID NO 18
<211> LENGTH: 21
<212> TYPE: DNA
<213> ORGANISM: Artificial Sequence
<220> FEATURE:
<223> OTHER INFORMATION: Synthetic Construct

<400> SEQUENCE: 18
actaaaaccc caatactccc a                                                  21

<210> SEQ ID NO 19
<211> LENGTH: 23
<212> TYPE: DNA
<213> ORGANISM: Artificial Sequence
<220> FEATURE:
<223> OTHER INFORMATION: Synthetic Construct

<400> SEQUENCE: 19
gtggatttag attaggattt tgt                                                23

<210> SEQ ID NO 20
<211> LENGTH: 18
<212> TYPE: DNA
<213> ORGANISM: Artificial Sequence
<220> FEATURE:
<223> OTHER INFORMATION: Synthetic Construct

<400> SEQUENCE: 20
caccctcccc aaattctt                                                      18

<210> SEQ ID NO 21
<211> LENGTH: 22
<212> TYPE: DNA
<213> ORGANISM: Artificial Sequence
<220> FEATURE:
<223> OTHER INFORMATION: Synthetic Construct

<400> SEQUENCE: 21
attaatagag ttttgtaaat at                                                 22

<210> SEQ ID NO 22
<211> LENGTH: 16
<212> TYPE: DNA
<213> ORGANISM: Artificial Sequence
<220> FEATURE:
<223> OTHER INFORMATION: Synthetic Construct

<400> SEQUENCE: 22
aagggtatgg gaattg                                                        16

<210> SEQ ID NO 23
```

```
<211> LENGTH: 15
<212> TYPE: DNA
<213> ORGANISM: Artificial Sequence
<220> FEATURE:
<223> OTHER INFORMATION: Synthetic Construct

<400> SEQUENCE: 23
tttgggattg ggaag                                                    15

<210> SEQ ID NO 24
<211> LENGTH: 24
<212> TYPE: DNA
<213> ORGANISM: Artificial Sequence
<220> FEATURE:
<223> OTHER INFORMATION: Synthetic Construct

<400> SEQUENCE: 24
tagtttaggg tatttttat ttat                                           24

<210> SEQ ID NO 25
<211> LENGTH: 24
<212> TYPE: DNA
<213> ORGANISM: Artificial Sequence
<220> FEATURE:
<223> OTHER INFORMATION: Synthetic Construct

<400> SEQUENCE: 25
gtgaaagtaa tgatatagta gaaa                                          24

<210> SEQ ID NO 26
<211> LENGTH: 15
<212> TYPE: DNA
<213> ORGANISM: Artificial Sequence
<220> FEATURE:
<223> OTHER INFORMATION: Synthetic Construct

<400> SEQUENCE: 26 tttggggtt gggga                                                     15

<210> SEQ ID NO 27
<211> LENGTH: 17
<212> TYPE: DNA
<213> ORGANISM: Artificial Sequence
<220> FEATURE:
<223> OTHER INFORMATION: Synthetic Construct

<400> SEQUENCE: 27
gggtgtttta ggtagtt                                                  17

<210> SEQ ID NO 28
<211> LENGTH: 19
<212> TYPE: DNA
<213> ORGANISM: Artificial Sequence
<220> FEATURE:
<223> OTHER INFORMATION: Synthetic Construct

<400> SEQUENCE: 28
cctcccaaac taaaatttc                                                19

<210> SEQ ID NO 29
<211> LENGTH: 15
<212> TYPE: DNA
<213> ORGANISM: Artificial Sequence
<220> FEATURE:
<223> OTHER INFORMATION: Synthetic Construct

<400> SEQUENCE: 29
```
tgggggtaga ggaga                                                      15

<210> SEQ ID NO 30
<211> LENGTH: 16
<212> TYPE: DNA
<213> ORGANISM: Artificial Sequence
<220> FEATURE:
<223> OTHER INFORMATION: Synthetic Construct

<400> SEQUENCE: 30
cctccccaaa ttcttc                                                     16

<210> SEQ ID NO 31
<211> LENGTH: 2000
<212> TYPE: DNA
<213> ORGANISM: Artificial Sequence
<220> FEATURE:
<223> OTHER INFORMATION: Synthetic Construct

<400> SEQUENCE: 31
actgcccttc tctcaatgat tcggattttg taacgggtt tgcaatttgc ttccggttgt       60
atttctcagg aagtccgatg acactcggct gtccaggcca ggcgctggaa gtcccccagg     120
aggaccagct cggtctccca cctcttgagt gcacagctcc ttggcccctg agtacccac     180 caccccatt tccagccttc ttccttacaa cacgaaggg tggaggaac cagaaaacag       240 gggatcccgc agccctaggc tagttctgat cgctttcagg tgtctgcaga ggcaagttgc    300
tggttgtcac ctgtaaaatg gggaggataa aaacacctcc cagattttgt tctagatcct    360 aggggatgt gaggctcaag ggagataaag gacactggag agcaccctag aaatgacagg     420
atgaaggcga tggtgacaaa tatccgagcg aaacgcttga caatgagaac agacaagtgc    480
aggtctccag gagtgccgcg agcgcccgcg ggttctgaga gcgctcaaag ccgccgagtc    540
aggctgccca gcccgccggg cctcgccgca gtgatcctca ttcccgaatc tggcagcgct    600
gtcaaaggct tgtattagga ggtgaacggc ggccgcaggc ccactccacg cggttgctga    660
aaccgagctg ggcgcgcgcg ggggccgaat ctcgccgcct ccgcgctcct gtcggggcag    720
ctcccgatcc cgggctgcgc ggcttcggtc cccaagacgg ccacttccag ccctaggccc    780
cttggccgca gcgcttccca aaccaagaga gatccttcct caactcagag cttttcatta    840
gcagtcgtta ataatggccc tgagttgcct tatcatctcc tggaaatgag aaataaattt    900
cttcggagaa cgtttccctt tgtaaaggac agagagtttt aaagatacag gtatgatgta    960
agacacataa ataccaggt aagcattagc agaaattctc ttttccttat atttaagtat    1020
aataaacata caagtgtagc tcaatgaatt ttcacaaact gacattctgt gtaaccagca   1080
gcctaagaaa ctgctttacc aacgatcccc tagctcgcct ccagttatgc acgccaataa   1140
ccactagcct aacttctacc acatgcccat tacttctgta gtttaaaact tctgattctt   1200
gaatgtaaac gtttaacaat aaatcgcttg aatttaactc aaatttcaaa tgtaagatga   1260
agtcagagat gcagcctgaa tctaggatca taatttgtct tgtgcggagg gcgagtaatt   1320
tccttgggca agaaaataac tggaggtgac agttgtttgg ggctgcagtc gtccgggcca   1380
ggagcacagg gcgggaagga atgccccatc tcttagggct ctctgcttgt cacctaccag   1440
gttggtcaga aacgttctca tcaaagcaat ggttctcttt tcttttctct ttgggacaga   1500
aggagtttct tgaccgccct cttccctgca aatgcataaa caaccactgc tcctgtctcc   1560
aagctcagat tcctaccaag atagccttt ctcttcccct ctcttttgta agtctcttga   1620

| | |
|---|---|
| tttcattctt tgaacctgtg attggaggtt aaagtgcacc aggttggaag gaggaagctc | 1680 |
| ttaacaataa aggtttgaat atttagctgt gtcaggtcgc tgccctctca cgagcctccc | 1740 |
| tcccctttat cttttaaaat gcaaattatg tttcgagggg ttgtgcgtag agtgcgcgct | 1800 |
| gcgcctcgac gtctccaacc attggtgtct gtgtcattac taatagagtc ttgtaaacac | 1860 |
| tcgttaatca cggaaggccg ccggcctggg gctccgcacg ccagcctgtg cgggtcttc | 1920 |
| cccgcctctg cagcctagtg ggaaggaggt gggaggaaag aaggaagaaa gggagggagg | 1980 |
| gaggaggcag gccagaggga | 2000 |

<210> SEQ ID NO 32
<211> LENGTH: 2000
<212> TYPE: DNA
<213> ORGANISM: Artificial Sequence
<220> FEATURE:
<223> OTHER INFORMATION: Synthetic Construct

<400> SEQUENCE: 32

| | |
|---|---|
| aggcgcgact gtgcgtgcgc agccgagggt ggtggcggcc ggcaccccac gccaagggtg | 60 |
| gtggtggccg gcaccccacc ctcggccgcc gcctccgcgt gtcaggtgcc gtgagaagcg | 120 |
| cgggaggagc ggccgcaggc agcgcccagg gatatgactg gagccgactt ccagaagcg | 180 |
| gcgcacgcaa agcccagctc cgcacgcaaa ggggaggcga cagcagaaac ttcaacccga | 240 |
| taaagttcgc cggagcgcgg agattcgcct cctcctgcca ctctccgccc cgctcgggtc | 300 |
| ccgccccgct agctccccca ggccccccca gtcgccccag cttggctccc cgccctgcgc | 360 |
| caacggcttc catcgcagcc tgggcggccc cgcgcccacc agcgggcggc gccacctgga | 420 |
| gtggcctcta cgcgggaaat ctcagggcca gctgcgcccc aggagccttt gtgtgcccaa | 480 |
| gcactgtcgg ggccccgggg cggggagcg gctactttta gggattcctg atctcgccgc | 540 |
| aagaactgga aaaatttag catgccaaag agcctccact gaggtggcaa tttgtttgcg | 600 |
| agaacctaag ataaaattta aacaaccaac caggggcgct gtgaggcaaa ccgctgccac | 660 |
| tacactggct ttccgggaag caagctcaag tcgcggagag ggaagggagg tcgtgcgctc | 720 |
| ggggcggggc gcgctcccaa gtcgagcgca gcggccgggg caggttgtac cgagcgtggt | 780 |
| tctggggaca ccgtgcggcc tcgattggag gtggctgtga tgaagcgcgg ttaccgcaca | 840 |
| atggaaacgt gggcacctcc gctcccatga aagcctgctg gtagagctcc gaggccggcc | 900 |
| ggtgcgcctg gacgggagtc cgggtcaaag cggcctggtg tgcggcgcgc cccgccccc | 960 |
| gcaggccccg ccctgccagg tcgcgctgcc ctccttctac ccagtcctta aaacccggag | 1020 |
| gagcgggatg gcgcgctttg actctggagt gggagtggga gcgagcgctt ctgcgactcc | 1080 |
| agttgtgaga gccgcaaggg catgggaatt gacgccactc accgaccccc agtctcaatc | 1140 |
| tcaacgctgt gaggaaacct cgactttgcc aggtccccaa gggcagcggg gctcggcgag | 1200 |
| cgaggcaccc ttctccgtcc ccatcccaat ccaagcgctc ctggcactga cgacgccaag | 1260 |
| agactcgagt gggagttaaa gcttccagtg agggcagcag gtgtccaggc cgggctgcgg | 1320 |
| gttcctgttg acgtcttgcc ctaggcaaag gtcccagttc cttctcggag ccggctgtcc | 1380 |
| cgcgccactg gaaaccgcac ctccccgcag gtcagtctgt ctgccgaggc gctgccggc | 1440 |
| gacctcttca gatggattat tacaggtagc gggtggcgtg gtaggtactt taaaggaaat | 1500 |
| caagcgccac cgcctcgatg cccgcagcgt tgtccccaga ttgcaggaac cgttacgcgc | 1560 |
| cttgcgggga ggggaagggt ttggcgctgg gttacagcga ggtggaaaca cgccccttct | 1620 |
| cttctccaag ggagagtggg ttggggatgg gaagggggcgt cttcggccat ttctccagag | 1680 |

```
agtcagctcc gacctctcca cccaacggca ctcagtcccc agaggctggg gtagggggcgt    1740 ggggcgcccg ctcctgtctc tgcacccctg agtgtcacgc cttctcctct ctgtcccccag    1800 catgggcacc agcctcagcc cgaacgaccc ttggccgcta aacccgctgt ccatccagca    1860
gaccacgctc ctgctactcc tgtcggtgct ggcactgtg catgtgggcc agcggctgct     1920
gaggcaacgg aggcggcagc tccggtccgc gcccccgggc ccgtttgcgt ggccactgat    1980
cggaaacgcg gcggcggtgg                                                2000
```

<210> SEQ ID NO 33
<211> LENGTH: 2000
<212> TYPE: DNA
<213> ORGANISM: Artificial Sequence
<220> FEATURE:
<223> OTHER INFORMATION: Synthetic Construct

<400> SEQUENCE: 33

```
caaaatgagt ttaagacgat ccttcccgag gcgccgcggt cactatagag agtgtctgag      60
gctgggctcc taccgcctgg ccttttggtg tctttggatc actggctatc tactcggggt    120
ctgtcactcc cgtgatcgcc taccttccag ggagacctag ggagggaga ccccaagacc      180 tgtcccaggt gaggccactt ggtcggcacc cggggctgca ggcacggcgc ccgcgtccgc    240
cctcgcccct taggctttcc attcgcgggc gaccccggtc gggccacctt agaatcgact    300
accctgcctg cctgactggt ctcgggctac aaactgtgtg gaagcgtagg tatctcactt    360
aactgctacc ccaaattcgg atttacaaac gactacgcag tcccgaatgc caacgcctt    420 ccctaaaccc agagataaat ctgggggaaa attcctcgcg gagcggaaaa caacgccagc    480
gtctaaagcg ttctgccccg agctggagtg gttcaaaaga caatgatctc aaaagaaagt    540
gattgttttg gtaatcccgg gaacagcttg caaggggag atttgggtct tcctttagta     600
acggaaagtc aatgcgcagc ctcctgtaat tatccttatc ggaagcccct tgtttaatct    660
gcatgtttag cggaggcccc actcgaacgc gcagcgagtg ggagacccac tttgcagggc    720
ccaggctcgg gctccggtcc ctgcgtgcgc gcaggcagcc gcgccgggtt cccgcggagc    780
tcaggcgttt gctcctcccct cgctgcggga cctcggactg taggaccctc agggagtggg    840
actgaggaga tctgcttccg gggttctggg attgggaagc ggggacgca gggctccgag     900 cgatgagggc tggttgggtt caaagcgcga accagtagtt acttacccac gtgcttgggg    960
ccaactttag cgaatatcag agtttcactg attattcaaa gaatcaggct ttctttgaat    1020
aatcgtgaaa ttgacaata aattgtaagc cccgatgaaa aggtgtgctt tccagtagac    1080
agactctatt ttatttcaat ttacctccct ccactcctcc ccaatttagg gttgctggat    1140
aaaatactga tacatactcc tacaaaaaaa aaaagccctc ctttttttatc tgaaatcaca    1200 tttcactgag ccgacagtgt tttgttggtt aaacctggta ccctgcccgt ctcagccccg    1260
ggcagtccac tcctctctct gcttctctcc ctttccccag ctcttgtgag tctgccaccc    1320
cctacagttc agcccgtgga gtgttgggga tggacctggg ggtggatttg gatggaggta    1380
gaatgaccat ggattaaagg gatggaggta ggatgaccat ggattaaata cacggttttc    1440 attccttttcc ccttggggat tttcagagaa ggccttctta caggaaggcc ttcgtggcac    1500
cggcggcgga ggtggagggc tggctgggga catatatggg gtagccatcg gggtgtggtt    1560
gggaatgggg tcctaggtct taataggcag ttgggtcgca tcaaagaagc ttcagggcag    1620
ctgggagtgg ggcctccacc cagagagtct ggaaggaagg agaaggccac gccaggatgt    1680
```

| | |
|---|---|
| agaacttgcg acttttcgag ggacaggcag acagcggagt cactgtccct taccttcttt | 1740 |
| cctcccctcc ctcctagaat gggggtgggg tgggtgggg tgggctggac agaagagagg | 1800 |
| aggagaagga ggtgactgag gggactgcag ctgggtgggc ggtaaccgag gggaggggaa | 1860 |
| ctggtggcgt ccccatctcg cggggtccgg aacggcgacg cgcccgcgcc cagctgattg | 1920 |
| gagcccttca ggcctcccgc gcccgaccgg cagcccaatc ctataaagct tcctctaagc | 1980 |
| tgggccctcc gcaaacggga | 2000 |

<210> SEQ ID NO 34
<211> LENGTH: 2000
<212> TYPE: DNA
<213> ORGANISM: Artificial Sequence
<220> FEATURE:
<223> OTHER INFORMATION: Synthetic Construct

<400> SEQUENCE: 34

| | |
|---|---|
| ttgtgataag caatccttgt aaaggtggtg gtggggggag gtggagagcc acataaacat | 60 |
| taatgctaat aaattagttt actcgactac agagtaatta cttcatatta ttgatattta | 120 |
| cagcaggtat tcaaatgcaa tggtaggcca ttatttggag aaaatacata ataagaatat | 180 |
| ttcttttcca gtgcaataca cgattagatt tgttattgag tcagttacag tcagctcagc | 240 |
| aataaataaa taaatcgatg ttgacactta aataccaaag atcttagagt ttatactcta | 300 |
| aatctcccca agatatgtaa ataactttgg ctatttcctg gagagggaaa acaaaaggt | 360 |
| tatctttta catattttt tattttcctt cagcaacatc ccagatcctt ccaagaagag | 420 |
| agttgttggg aggcctcagg tctgggcct tctcagctcc tggctctgcc tggctgctct | 480 |
| gtgctctgtg tcctctcctt tctttcgctt cctccaaaca ttgctccttc aatcctgcag | 540 |
| gatggggagc atattttgcc ttcttaattt attttttttc ctcttctcaa gaaagctaga | 600 |
| ctcagagtat tgctatggcc tctctctatc cttagcacaa acctagcttt ttaaagacat | 660 |
| ccctgttttcc ccaggtgcag ggagttcggg aagcacctct cctttctctg gtattgtatt | 720 |
| cctcctgtgg aatgagcagt aggaaaggca cagagctctc tgagttttg ccctgcacat | 780 |
| cccttgcttt cactctcaca cattgcaagg aaggagagta ggagagtagg tgggttaccc | 840 |
| ctttctcagc cacctctcct tggccctcag cccgtccttt ccacctccat tctccccaca | 900 |
| cccctggagc tctgtaagca gcctgatggg cccccacga agatgcagca tacccaggag | 960 |
| aagtctcctc ggatgtcagc gcctctaaag cagcccaagg cttgcctcaa ttgcatggtt | 1020 |
| tcccgagtcc tcagctccag aagaccaggc agatgggtgg accggtgagc agcagggcag | 1080 |
| cccctgtgcc tctgtctctg ccgagtcact ccgaagcccg gcaggcagcg aggaggaggg | 1140 |
| agtttctcca aggacagaag gtgggatgaa gaggtaggca gggaagatga ggggagaggt | 1200 |
| ggatcccggg taagacgaag gcccttccgg gccctgcgga tcagtgacaa accgcgggga | 1260 |
| gaagccgttc tggctgttgg cggtttaggg acggaaggca ctaaagcgct tcggaagtga | 1320 |
| ccatgaatga gagagtgtaa tcaagtcacc gtgcaaatcg acaagccac caggcaggca | 1380 |
| catccacggc ttcaaactct ggccccgaag gggttccggc tagggtcgga ggcagaggcg | 1440 |
| cttcccagag caagtctatg ggagggac tgcgaagaag ggggtgcaaa tgcgagactc | 1500 |
| caggagaaca gactccgaga ccacaggcca cacagcgacg gactcccacc tggctatccc | 1560 |
| cagtccaggg catccctcac ccacccgggg agctgcgggt gggaggtggg gacgagagtt | 1620 |
| gagctctcac cgcccctctgc acactcgaga acgaggaccc tgcaattgag cacaagcatg | 1680 |
| ctgcatgggg gcgcacccca gcctctccgc gcgcgccggg aggccccca gccaacatga | 1740 |

```
gttacaccgg cgattacgtg ctttcggtga gaacaccgag tgacgatctg ttgcttcccc      1800
tgaggtggct acaagaaag gaagccggga gggaggggag aggaggaaaa aaaaaaaagg      1860
aaaggggggg ggaaaaggcc cggactagct agcagcttgt caatttcaac atcgggtcac      1920
atgaccagca cctccctgct aaggatgggg atagatttcc acgtcagctt acgtctccaa      1980
atttctactt cacggatccg                                                  2000
```

<210> SEQ ID NO 35  
<211> LENGTH: 2000  
<212> TYPE: DNA  
<213> ORGANISM: Artificial Sequence  
<220> FEATURE:  
<223> OTHER INFORMATION: Synthetic Construct

<400> SEQUENCE: 35

```
agcttcattg ttgcctgctt ctaaagataa atggctttgc ttttcagaa gggattgggc       60 ccaggaaaac tgcctctctg ggagtcgagt ggggtgtgtg tgtgtgtttt cttataaaat      120
gtttcaagca tgttttcggt gggacagttg catcctgagg cccagccata aggctttgtc      180 ttgttttct ctgaatggct gggcttgcca aggagagata gaccctggga gcgaaacagc       240
tggcggtgcc tcagccctc tttcctccca aggaagcgca ttgttattaa ctgggaattc       300
tttatagccg ggctggagga agttttggct gtaaactgtc atgcactgca gccttcgctg      360
aaaaggcgga gggagtgggc ctggtcctgg gaaccgagga acaaagatca gaaaatcagc      420
cacagaaagg ggaggaaaaa taacgttag aaagtgaaga caggtgacac tacacaagtg       480
ctggccaaag tcggtgactt ccaacctcta cctcctccga cttgggtggt tcaattcctg      540
ggtcgtactc ttcaatgctt cagacattct ctctggagag tagaaatttt attacgcgtg      600
ttagaaacgg aatattcttt cctgctgaag ttgtattctt atttggccgt gccctcctg      660 ttcgaaacag ttttagagcg atctgttaaa ccctccagtc ttctttggcg cttcccgact      720
gtgggaaaag cggccgcgac gccgtccgag cgcagggag ggatccagcc ttcgggactc       780 cttttgccctg aagccgcagg agaggtttcg ctcccgtgcc tagggttccg aggccctcaa     840
ttgcctggga cccacccctcg ttcctccttc acctcccctc cacttttccc ttttatctta     900
tcctcgggag gccttgggcc aaagcgatga cctcttagac atttttaatac ccggagtaag    960 gagagtaaca cgcaccacgc tctccccaa agcccaggac ccgatgagcc agtgaaggcg      1020
tgtcaggagg gtccggcgtc aggagcaaat gaggtccttt tggtgcctct ttctagaagg     1080
aaacttcccc acctcgggtc agcccctg gaatatccat gcatcccaga catcaaaaga      1140
cactgagaaa tgcggacagg gactagacgc tccggcttcc tgactcgtcg gtgtaagttg     1200
gagaagggag agaaggagcc ctgtccccca cgggcggcag gcacccttcc ccgggactgg     1260
ctcctggcag ccctccgcat accgcgaggc gggtcgatcc ctcgagtccc gggcgggat      1320 cccctcttcg gcttccccag caattcccga ccccggagcg agcccggctg gcgaggggc     1380 gaggggcagg gggcaggggg caggggagac ttagcgcggg gcgcagatac catgtccgcg    1440
ggaaagcccc cttgctaggg cgcaagactc ctctgaactc gctgccccac ccgatgcgca    1500
ggctttctct agaggggttg gggctgggt gcccgctcag gagaccggga acagaggct      1560 gctacccgag gcaggccctc gtccagcgaa tgggcgaggt gtgcagaagc gcaaagccag   1620
gccttggaag ggggagcttc tgcctccttc cccttcctg ggctcccgtt ttaggaggaa     1680
tgttactgtt taaagagacc ccactgaact atttcctgct cattgtcacc tctccttcgc     1740
```

| | |
|---|---|
| tctcctcgcg taagttctca ccgaaaggta ataaaacaac cgctgccgac accgcttggc | 1800 |
| gctgggccgg gcggggaaag cgccccgagt cccactagtc cggaccaccc cgccagcccc | 1860 |
| gaccttctcc caccttccgt gaaagcaatg acacagcaga aaccacgcac acgcctggca | 1920 |
| cactcgatgc gcgcgctgac ctcggcaaca agtcctgttt ttataagaga gcgaggagga | 1980 |
| cacttctcag aagggggttgt | 2000 |

<210> SEQ ID NO 36
<211> LENGTH: 2000
<212> TYPE: DNA
<213> ORGANISM: Artificial Sequence
<220> FEATURE:
<223> OTHER INFORMATION: Synthetic Construct

<400> SEQUENCE: 36

| | |
|---|---|
| ataataacag ccagtattct tcccacatac ttccggtcaa aagtggggaa accagaaacc | 60 |
| gaataaaaca ttgggaagag acatactgtg ttcctggaaa aaatataaca gagccagatt | 120 |
| taactcggtg agagggaaag tgaccccctt gagaaaccag ggaatgtctc accctcagac | 180 |
| caacccttc ttttgcaaat tgaattggtc aaagtttagt tttgtcatca tttctattgt | 240 |
| tataattctt attcattttc ccagcccgt ccacacttct atttttcact accccacgc | 300 |
| cccacaagtt gccaccgggt caggtgggga catatccgga gagaaataga aagggatgca | 360 |
| ttttaaagcg agttctcttt tgagaggaaa acaatgggta gttttggaag tgtctttctt | 420 |
| aaaaacggaa ggagaaggtg aagaaaaaaa ttatcaacag caatgggccc ctttggtttg | 480 |
| ggttttgact tttaaagag gaacctctgc tgtcctgttg cagtattaaa atcagggcag | 540 |
| gaattttgca aaatgagaaa aataaacttc gggagaaaac ccagctggga gcagcttcgg | 600 |
| gaaagcgaca gttctccgaa aggaggaagg gaggatgcgc gctgtagccg gctccggagt | 660 |
| ttactgcccg aacgattggg gaaaagaacg aggattctca aatctagttg cgatctctcg | 720 |
| tctctccttt attctgttcg tggtgcgggc ttcggagcgt ctgggaaagc cagtctgtga | 780 |
| agctggactt gcagaatcct ttgaatgccg gtccaggtgg ctgcagggcc cgcagtccgg | 840 |
| gatgccggag aaaggaacca caaggaaaag acgctacgct cggagtttcc ccttttcctt | 900 |
| gcagccccgg cggggcctag gcctcggttt ccggcccacc tcggctcaga ggtcaagtag | 960 |
| gaactcatct cgtcgaccta gggtttggga gaaggatttc gggttgcgtt cttggcatct | 1020 |
| gggagcaaac acgagcctcg gatttgggga catatcgtta ttaacagctt gggaaacgaa | 1080 |
| agcgaagctc ggggcagcca ctgcagcctg gctgagagaa aggacgcggg ttgtgctctc | 1140 |
| tggaagcaaa ggggtctgcg gcccagctgg cctgggagct tgtggccggc gctggaagct | 1200 |
| gcccgctctc cccgcgggcc tgaccttggc tcccgccgca gctctgccgg ccgactgcct | 1260 |
| ccctgcacat tttgctgccg ttccagtcct tacaggaccg ggcctggagc caggccatgc | 1320 |
| ttcggaaagc cctgggggtt ggggacgcgc aaaacccaga atcgaacccc gaagctgggg | 1380 |
| gcaagtccag attcagacgt ccagctccct cgggacccct tggcggagaa cttacccttc | 1440 |
| cggaaggccc gacgctctcc ggctctgtgc tgggcaggcc tagctcttct ctcggcgcca | 1500 |
| ccaggggcgt ctacgcggta cgttttgcaa ctcaacctag tgggtttcca gcggtgcgca | 1560 |
| aaagtttgcg agcatccacc actgcgctgc ttagaaattg tgcccattga tcagactaaa | 1620 |
| aataatagtc gtcgtgatta caaaacaaaa tagagtgcct cgtgcctcgg cgggccctgg | 1680 |
| tacaataatt attctctaca gaaaccacct ctctccactc ccaccctac tccaccaccc | 1740 |
| actcgcaccc cgcccctgcc gggccactct gggacgaatt gcattcttgg acctttctct | 1800 |

```
ccgcaaggca cattacggag aactccctct gtctcgtgtc ccctccacga caacccagta    1860
attatttcta tgcaagtctg caagagggca ctgagttatc gcatcccaag cctaaccagc    1920
tagagcggcg cctcggtatt catttgccca gagctcctcc gcgggggatt taaaaataat    1980
aataataata ataaggatcc                                                2000

<210> SEQ ID NO 37
<211> LENGTH: 2000
<212> TYPE: DNA
<213> ORGANISM: Artificial Sequence
<220> FEATURE:
<223> OTHER INFORMATION: Synthetic Construct

<400> SEQUENCE: 37
agcgactgta gaaatcagcc ctttgcagag ggcgcagagg gcctggaaac ctctgggacc      60
ttttcccagg aactgtttat ggtttccccc taggtctagg agacatagat gcataggtgg     120 attgataca tcgatggtag ctataaggta agcagacaat ggtcacagat ggaaaggtgg     180
acggacggat gacggatggt tagaagatgt tttgagggct tgctatagtg ccaggcacaa     240
ggctaagaga tttcgtccac tatttcattt gattctctcc agaaccttat gaatggcata     300
ttacctctgt tcctattttt caaatagggg aactgaggcc tcaggcaatg taagcagctt     360
gccgcttagc aatcttttgc agagccagga agcgggaaag cgtgtcttaa tggacagtac     420
cagcctccac agtgtgccct cggccccctc ccggtggaga agaggttcca agccccggcg     480
tcccgggtag ggtgtccctc atccctccct ccccaccaca ctcctggcgc gctgacatta     540
cacccgcccc ggcacccccc tctcactgat ccaacacccc cggacaccct ggacagcgct     600
ctcaaggcag taggtcttcg acttgggagc cccggggagc tggttaaaca cggatcctct     660
cccacagtgg ctgaaaagcg cgcagtcccg gaacctgagg gtttacctgc ttctacgctt     720
ggccaagggt ctctaactgg aaaggtgaaa attctgtcct gagattttaa gattcccaga     780
aactttcaat cgttcagttc ctgtaaccat taattgagcg cctaaactgc gcaccttgac     840
gctgttagat gctgcagtaa ggaactcgga gtcaagtgtg ggggacaggt tggtcaataa     900
atgacgacat tccggacggc tgtgcttggt gcccacgggg accgcgagg gggcccaggg     960 aggaggcggg aaaggggcag gttcaccggc ccgctgggtc tccagcacat tccagaagtc    1020
taagccagtc catctatcct tccaaacgcc cccacctcgc ttccctccct ggagcccgca    1080
tcccacggtg caatttcagt gactttatgc ggagaaactt gatcctatct cactctcccc    1140
aaacttccta actgccttgg gtttgtcacc tggccgtgtg gggagccacc gagcgccccc    1200 tgtggcccccc acccgagctc ggcgggggga gcggcgcgcg ggtgctgggg gaccgacccc    1260
tcccgcgaag gcgtcggcgc ggggctggcg tagggcctgc gtcagctgca gcccgccggc    1320
gattggggcg cgcgcgcctc cttcggtttg gggctaatta taaagtggct ccagcagccg    1380
ttaagccccg ggacggcgag gcaggcgctc agagccccgc agcctggccc gtgacccgc    1440 agagacgctg aggaccgcga cggtgaggcc ctacgtccgc cagcacaccc gggcccgctt    1500
ctccccgacg cccgccctcc tcacacttgc cttcttctct tccctctaga gtcgtgtctg    1560
aacccggctt ttccaattgg cctgctccat ccgaacagcg tcaacgtgag tgaatttgcc    1620
cgaagcttgt ctttgctgag cgggtttggg gacgtctgcc cgccctcttt cccttcacat    1680
ttcattgcat gggttcccca acagcgttcc ctggttcttc tttgtgaccc cagtcaatgt    1740
cctgcctccc ccggctcccg ctctctcgcc cctggtctgc ggcgttctct ccggaatctt    1800
```

| | |
|---|---|
| gccctgggcc gcggacgccc aggaaaagag ccgggtgccc caggcagcct cgcgttgggg | 1860 |
| gcgaccgcgc catcccggga accgcgaggc gatctgagtc gcctccacgt ctacctaaaa | 1920 |
| gctgtcggcc gggagggcgg ggccccagaa aggagcattc ctgcgggctt ttgctcgacg | 1980 |
| atcccctgct gaggctgtcg | 2000 |

<210> SEQ ID NO 38
<211> LENGTH: 2000
<212> TYPE: DNA
<213> ORGANISM: Artificial Sequence
<220> FEATURE:
<223> OTHER INFORMATION: Synthetic Construct

<400> SEQUENCE: 38

| | |
|---|---|
| gtatacttca gagagaagac tgaaacttct agagactgtt tctagcatcc ttaagtaact | 60 |
| gcagacactt ataatactga atgatatcct agttataaat aattcttatc cataacttaa | 120 |
| atccatcttg aggctctact aagtaaatct tccttaacct acttagagga tgtgcagtag | 180 |
| cgatgaaagt agcctttctt ttctttttt tttttttttt ttttgagacg gagtctcgct | 240 |
| ctgtcgccag gctggagtac agtggcgcga tctcggctca ctgtaacctc ctccgcctcc | 300 |
| tgggttccag cgattctcct gcctcagcct cccgagtagc tgggactaca ggcgtgcgcc | 360 |
| accactccca cataattttt tgtatttta gtagagacgg ggtttcaccg tgttggccag | 420 |
| gatggtctca atctcttga cctcgtgatc tgtgtgctgg gagtacaggc gtgagccacc | 480 |
| gcgcccggcc ttaagcccct ttctttaagg ctcaagggca tattttcaca ctgcagtgca | 540 |
| tcacaaccgt tttcattctt ccagtgttcc tttcttctgg tctccagcca cctgccaggt | 600 |
| acttctgatt aattacatat aagatttatc caagccaccc cctccgtttc taccaactgg | 660 |
| acttcattct cttcagttcc tgctagaatg cacctcctac ctgaagtctt ccctcatcaa | 720 |
| tgccctccat gatcagcctt tgactctgga atcccttaat atattcctca gatcattaga | 780 |
| ggttttctga gtcatcatct gagattttc attaaattgt ggagtttgag cagccagtcc | 840 |
| tgagctgtcg gactcagttc caaatagaag tcctagttaa agacacaaaa acaagaagat | 900 |
| gggttagctg cggctcgaag agctggtgag cgcgaccaca gggcagcttg cggacggttc | 960 |
| tttcggacag dacaagggcg agggaaacgg cagaatggtg acgcacctga gtgcgcccac | 1020 |
| tagacgaaag aagaccaact aagccttcgt gtagtgcgta gacaggccga cacacacaca | 1080 |
| cacacacaca cacacacact aacacacacg caaagacagt gagggagcga gaggcgcatc | 1140 |
| cccaggtagc tgacaatgac acggcccga tccggacgcg ggcttaaagc cccccgactt | 1200 |
| ccggagtgcc cccctccccg gcgacctccg gagattaccg ctggcgcatc tctccgccct | 1260 |
| gcccggctcc ggcgccctcc cctcccccg cagccgcagc tccccgcccc ccgcgaacgc | 1320 |
| ggctccccag tgtcctccag aacgcccgcg tggctgtcgg gtttcgaacc ccagggccga | 1380 |
| ctctagtact cggcgcgcgc gccgccgcgt cgccgaccag cctgcggccc ccgcatcaat | 1440 |
| cattaacggg gcggcccggg ctgcggcggc ccgaggaggg ggatggtacg gaactcgaga | 1500 |
| caggggacaa ctctatcccc cgaagcggcc gcgaaaccct agcctgggag gccccgcccc | 1560 |
| ttcctcggtg cgcccgtccc tccctccgcg cctcggctcg cacatcccca cctcccgctc | 1620 |
| cgggggcggc ggcggcggag gcacccgcac cgcgcgatgc ccagtcaccg ctgccgcgct | 1680 |
| gccgccgcag tcagccgcgc cgccgccgct ggcgcagccg gggcggccgc gcgccggtag | 1740 |
| caggggcttg gcgaggaagc cgctgagcct cgcgcgctcc gcgctcctgg cggtcgcagc | 1800 |
| gctgcctatt aattgattct cttattgatt tatttaattt ttaggagcgg ctgctcggag | 1860 |

| | |
|---|---:|
| gcacgggtct tctcctaaac ctgcagcgac gccccggcg tgggcacaaa ggctccgacg | 1920 |
| gcggccggcg ggggctgccc agcgcccggg agccggcgcc agaggtcgcc tgcgcgcgcc | 1980 |
| ctagccgagc cccgggcacc | 2000 |

<210> SEQ ID NO 39
<211> LENGTH: 1000
<212> TYPE: DNA
<213> ORGANISM: Artificial Sequence
<220> FEATURE:
<223> OTHER INFORMATION: Synthetic Construct

<400> SEQUENCE: 39

| | |
|---|---:|
| ttcatcttaa agaatctgag ttgaatagag agggaaatga ggggcgggtg ttcgctccaa | 60 |
| cgaaatcgct tggaggatca tggggcgtgt gtccctgtgt gcggaactgg gaggaaaacg | 120 |
| cagcccccag tttggtaaat ggtgaagcag cggtaggccg gtcggtggcg cggatttaag | 180 |
| atttgctgaa ggcactacca cagatgtagc tctctggaac ttccatccct cctctcctac | 240 |
| cacccccaa aaaagacaa aaccgagttc agaccggctc cccaacacc aagccgcttc | 300 |
| tatttatcaa gtgggtcaac ttccactcgg aagcacctcg cggggctcgg ctccagggca | 360 |
| cctggtggct ggggagctgt attgttttcc tgggcacgga ggttcggcgc cggttttagg | 420 |
| attgtgcaaa aagagagtag aaggtacaga gatttatttc tgcttttgc tgttcagccg | 480 |
| ccgtttgccc cagcgaggtg ggctggaggc tgaatttcaa gccttgttta acctctacaa | 540 |
| gagacaccct ccattcagcc atctcacttt ctctctggcc tccctctctc ttttttcct | 600 |
| ttccgttctc tccgtccttt ctctctatct ctgtctctgt gtgtgtcgtg tttgttcccg | 660 |
| tgccctcctc tccgaccttg gccgggctc ctagtcctga gagaaacggc gttcggtgcg | 720 |
| ccggcggtgg ctatgcggct ggctctttcg gggctcccgg gactaggttg gggaaagagg | 780 |
| gcatctcccc ggcctctcgg ggcccagccc agtcttccta gatctggcgt ccgcccttcc | 840 |
| ctcccctccc gcactggcag gagagaaatg gccgcagtgt gggccgcggg gcagctagga | 900 |
| ctggaaagcg gggaccctgg agggtgcgat cgcggacggg gtgtgcgggc gcgggtcgtg | 960 |
| tgcgtgtgcg tgcagggttc cgaccacggg gacacgagct | 1000 |

<210> SEQ ID NO 40
<211> LENGTH: 1000
<212> TYPE: DNA
<213> ORGANISM: Artificial Sequence
<220> FEATURE:
<223> OTHER INFORMATION: Synthetic Construct

<400> SEQUENCE: 40

| | |
|---|---:|
| gtggagggcg ttggaccttc ttccgcaatc gggaccactc caggtctccc cggagaaggc | 60 |
| tgagtctcca gcgcgtggat tcagatcagg actctgtcta agtaggcgag agctggggat | 120 |
| accgctgggg gctttggcga agctaagaaa gcactggctt cttattctca ccagacatct | 180 |
| caacacccac gtgcgctggg tcccgcagtc tctcgcccgc cccacgcggg tcccagccct | 240 |
| ggtccttact ccccgcgcgg gaagaatctg ggagggtgg gggcggagag gcggctgatc | 300 |
| ggagagtgg agggaggatg ggagatgggc agaggctgcc cgcatcaggg ccaggacaga | 360 |
| cgtccgcgcg gccccaggca ctcacttgag tgtcacgcaa gtcaccccaa caccgcacaa | 420 |
| gacagtggcg gggtgcgcac cgaggcccct acctgggggg tgtgcgcgca ctgaacgacc | 480 |
| ccttctccag gtgcgcgagc cgctccggcg gccgtgcaca ctgcgccccc ttccgcccac | 540 |

```
ctgcctggcc tgcgtttcta accacgcggg cggtcccgag acttcgcgca aaaggcagga       600
ccgcgactcc caataatgat atcttcgaaa taacccoctg ctgagccggc gcccagggcc       660
gggggtagag tcccgagtcc cttttgcgga attaaggaga cctctggcga ccggggagcc       720
tgcccctgtg accgctccag cagcccctgc cgcgtgcgtg cccgagtgtg gcccgcagct       780
cccaaagccc aggtgtgtgt ggcctagggc ggggagagtt ggcgaccegg gcccatcacc       840 gccccagtgc caccgcccca gtgcctgacc agatggggtg cggtccctac gcccggcgtg       900
gccccgccgc cgctcagatc tgaagtccgg ctttcgctcg ccctgcgcgg cggaacctct       960
gacccggagc agctctaggc cgtgggcttc gtctcctcct                            1000

<210> SEQ ID NO 41
<211> LENGTH: 30
<212> TYPE: DNA
<213> ORGANISM: Artificial Sequence
<220> FEATURE:
<223> OTHER INFORMATION: Synthetic Construct

<400> SEQUENCE: 41
ttcttattct caccagacat ctcaacaccc                                         30

<210> SEQ ID NO 42
<211> LENGTH: 25
<212> TYPE: DNA
<213> ORGANISM: Artificial Sequence
<220> FEATURE:
<223> OTHER INFORMATION: Synthetic Construct

<400> SEQUENCE: 42
atctcccatc ctccctccca ctctc                                              25
```

DIAGNOSIS KIT AND CHIP FOR BLADDER CANCER USING BLADDER CANCER SPECIFIC METHYLATION MARKER GENE

CROSS-REFERENCE TO RELATED APPLICATIONS

This application is a divisional application of and claims the priority of U.S. patent application Ser. No. 12/744,491 filed on Jun. 24, 2010 entitled "DIAGNOSIS KIT AND CHIP FOR BLADDER CANCER USING BLADDER CANCER SPECIFIC METHYLATION MARKER GENE" in the name of Sung Whan AN, et al., which claims priority of International Patent Application No. PCT/KR2008/007081 filed on 01 Dec. 2008, which claims priority of Korean Patent Application No. 10-2007-0124015 filed on 30 Nov. 2007, all of which are hereby incorporated by reference herein in their entireties.

TECHNICAL FIELD

The present invention relates to a kit and nucleic acid chip for diagnosing bladder cancer using a bladder cancer-specific marker gene, and more particularly to a kit and nucleic acid chip for diagnosing bladder cancer, which can detect the promoter methylation of a bladder cancer-specific gene, the promoter region of which is methylated specifically in transformed cells of bladder cancer.

BACKGROUND ART

Bladder cancer is the most frequent cancer of the urinary system and was found to be caused by many factors. It is known that bladder cancer is mainly caused by smoking or various chemical substances (paints for leather, air pollutants, artificial sweetening agents, nitrates and the like) which irritate the bladder wall while they are excreted as urine after being absorbed in vivo.

As conventional methods for diagnosing bladder cancer, a method of finding abnormal cells in urine is used, but has low accuracy. Also, cystoscopy comprising inserting a catheter into the bladder and collecting suspected tissue from the bladder is an invasive method having relatively high accuracy.

Generally, when bladder cancer is diagnosed at an early stage, the survival rate of bladder cancer patients is increased, but it is not easy to diagnose bladder cancer at an early stage. As a method for diagnosing bladder cancer, a method of incising part of the body is currently being used, but it has difficulty in diagnosing bladder cancer at an early stage.

Bladder cancers are classified, according to invasion into the muscular layer of the bladder, into superficial cancer and invasive cancer. Generally, about 30% of patients upon diagnosis of bladder cancer are invasive bladder cancer patients. Thus, in order to increase the survival period of patients, it is the best method to diagnose bladder cancer at early stage when the bladder cancer lesions are small. Accordingly, there is an urgent need to development a diagnostic method more efficient than various prior diagnostic methods for bladder cancer, that is, a bladder cancer-specific biomarker which allows early diagnosis of bladder cancer, can treat a large amount of samples and has high sensitivity and specificity.

Recently, methods of diagnosing cancer through the measurement of DNA methylation have been suggested. DNA methylation occurs mainly on the cytosine of CpG islands in the promoter region of a specific gene to interfere with the binding of transcription factors, thus silencing the expression of the gene. Thus, detecting the methylation of CpG islands in the promoter of tumor inhibitory genes greatly assists in cancer research. Recently, an attempt has been actively made to determine promoter methylation, by methods such as methylation-specific PCR (hereinafter referred to as MSP) or automatic DNA sequencing, for the diagnosis and screening of cancer.

Although there are disputes on whether the methylation of promoter CpG islands directly induces cancer development or causes a secondary change after cancer development, it has been found that tumor suppressor genes, DNA repair genes, cell cycle regulatory genes and the line in several cancers are hyper-methylated, and thus the expression of these genes are silenced. Particularly, it is known that the hyper-methylation of the promoter region of a specific gene occurs at an early stage of cancer development.

Thus, the methylation of the promoter methylation of tumor-associated genes is an important indication of cancer and can be used in many applications, including the diagnosis and early diagnosis of cancer, the prediction of cancer development, the prediction of prognosis of cancer, follow-up examination after treatment, and the prediction of responses to anticancer therapy. Recently, an actual attempt to examine the promoter methylation of tumor-associated genes in blood, sputum, saliva, feces and to use the examined results for diagnosis and treatment of various cancers has been actively made (Esteller, M. et al., *Cancer Res.*, 59:67, 1999; Sanchez-Cespedez, M. et al., *Cancer Res.*, 60:892, 2000; Ahlquist, D. A. et al., *Gastroenterol.*, 119:1219, 2000).

Accordingly, the present inventors have made many efforts to develop a diagnostic kit capable of effectively diagnosing bladder cancer and, as a result, have found that bladder cancer can be diagnosed by measuring the methylation degree using as a biomarker the promoter of methylation-associated genes which are expressed specifically in bladder cancer cells, thereby completing the present invention.

SUMMARY OF INVENTION

It is, therefore, an object of the present invention to provide a kit for diagnosing bladder cancer, which comprises the methylated promoter or exon region of a bladder cancer marker gene.

Another object of the present invention is to provide a nucleic acid chip for diagnosing bladder cancer, which comprises a probe capable of hybridizing with a fragment containing the CpG island of the bladder cancer-specific marker gene.

Still another object of the present invention is to provide a method for measuring the methylation of the promoter or exon region of a gene originated from a clinical sample.

To achieve the above objects, the present invention provides a kit for diagnosing bladder cancer, which comprises the methylated promoter or exon region of a bladder cancer marker gene selected from the group consisting of: (1) CDX2 (NM_001265)—caudal type homeobox transcription factor 2; (2) CYP1B1 (NM_000104)—cytochrome P450, family 1, subfamily B, polypeptide 1; (3) VSX1 (NM_199425)—visual system homeobox 1 homolog, CHX10-like (zebrafish); (4) HOXA11 (NM_005523)—homeobox A11; (5) T (NM_003181)—T, brachyury homolog (mouse); (6) TBX5 (NM_080717)—T-box 5; (7) PENK (NM_006211)—proenkephalin; (8) PAQR9 (NM_198504)—progestin and adipoQ receptor family member IV; (9) LHX2 (NM_004789)—LIM Homeobox 2; and (10) SIM2 (U80456)—single-minded homog 2 (Drosophila).

The present invention also provides a nucleic acid chip for diagnosing bladder cancer, which comprises a probe capable of hybridizing with a fragment containing the CpG island of the promoter or exon region of the bladder cancer marker gene selected from the group consisting of: (1) CDX2 (NM_001265)—caudal type homeobox transcription factor 2; (2) CYP1B1 (NM_000104)—cytochrome P450, family 1, subfamily B, polypeptide 1; (3) VSX1 (NM_199425)—visual system homeobox 1 homolog, CHX10-like (zebrafish); (4) HOXA11 (NM_005523)—homeobox A11; (5) T (NM_003181)—T, brachyury homolog (mouse); (6) TBX5 (NM_080717)—T-box 5; (7) PENK (NM_006211)—proenkephalin; (8) PAQR9 (NM_198504)—progestin and adipoQ receptor family member IV; (9) LHX2 (NM_004789)—LIM Homeobox 2; and (10) SIM2 (U80456)—single-minded homog 2 (Drosophila).

The present invention also provides a method for detecting the methylation of the promoter or exon region of a clinical sample-originated gene selected from the group consisting of CDX2, CYP1B1, VSX1, HOXA11, T, TBX5, PENK, PAQR9, LHX2 and SIM2.

Other features and embodiments of the present invention will be more apparent from the following detailed description and the appended claims.

BRIEF DESCRIPTION OF DRAWINGS

FIG. 3(A) shows measurement results for the methylation degrees of the CDX2, the CYP1B1 and the T biomarker genes in the urinary cells of normal persons, Cystitis patients, hematuria patients and bladder cancer patients.

FIG. 3(B) shows measurement results for the methylation degrees of the TBX5, the LHX2 and the SIM2 biomarker genes in the urinary cells of normal persons, Cystitis patients, hematuria patients and bladder cancer patients.

FIG. 3(C) shows measurement results for the methylation degrees of the VSX1, the HOXA11 and the PENK biomarker genes in the urinary cells of normal persons, Cystitis patients, hematuria patients and bladder cancer patients.

FIG. 3(D) shows measurement results for the methylation degrees of the PAQR9 biomarker genes in the urinary cells of normal persons, Cystitis patients, hematuria patients and bladder cancer patients.

DETAILED DESCRIPTION OF THE INVENTION AND PREFERRED EMBODIMENTS

Figure 1:
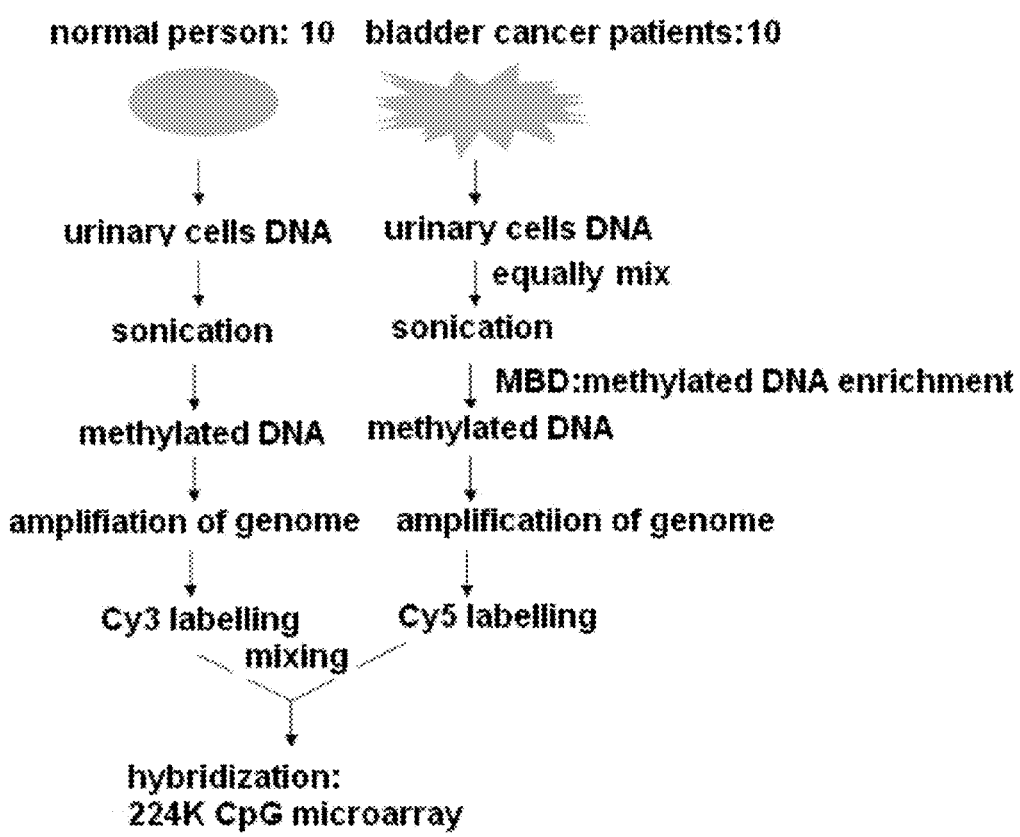
FIG. 1 is a schematic diagram showing a process of discovering a methylated biomarker for diagnosis of bladder cancer from the urinary cells of normal persons and bladder cancer patients through CpG micrroarray analysis.

In one aspect, the present invention relates to a kit for diagnosing bladder cancer, which comprises the methylated promoter or exon region of a bladder cancer marker gene.

In another aspect, the present invention relates to a nucleic acid chip for diagnosing bladder cancer, which comprises a probe capable of hybridizing with a fragment containing the CpG island of the promoter or exon region of a bladder cancer marker gene.

In the present invention, the promoter or exon region may contain at least one methylated CpG dinucleotide. Also, the promoter or exon region is any one of DNA sequences represented in SEQ ID NO: 31 to SEQ ID NO: 40.

In the present invention, the probe preferably has a size ranging from 10 bp to 1 kb, and has a homology with a base sequence containing the CpG island of the promoter or exon region of a bladder cancer marker gene, such that it can hybridize with the base sequence. More preferably, the probe has a size of 10-100 bp, and has a homology with a base sequence containing the CpG island of the promoter or exon region of a bladder cancer marker gene, such that it can hybridize with the base sequence in strict conditions. If the size of the probe is less than 10 bp, non-specific hybridization will occur, and if it is more than 1 kb, the binding between the probes will occur, thus making it difficult to read hybridization results.

A method for screening a methylation marker gene according to the present invention comprises the steps of: (a) isolating genomic DNAs from transformed cells and non-transformed cells; (b) reacting the isolated genomic DNAs to with a protein binding to methylated DNA and isolating methylated DNAs from the genomic DNAs; and (c) amplifying the isolated methylated DNAs, hybridizing the amplified DNAs to CpG microarrays, and selecting a methylation marker gene showing the greatest difference in methylation degree between normal cells and cancer cells among from the hybridized genes.

By the method for screening the methylation biomarker gene, it is possible to screen various genes, which are methylated not only in bladder cancer, but also in various dysplasic stages which progress to bladder cancer. The screened genes are also useful for blood cancer screening, risk assessment, prognosis, disease identification, disease staging, and selection of therapeutic targets.

The identification of the methylated gene in bladder cancer and abnormalities at various stages enables early diagnosis of bladder cancer in an accurate and effective manner, and allows establishment of methylation data using multiple genes and identification of new therapeutic targets. Additionally, methylation data according to the present invention enables establishment of a more accurate system for diagnosing bladder cancer, when it is used together with a method for detecting other non-methylation-associated biomarkers.

The inventive method enables diagnosis of bladder cancer progression at various stages by determining the methylation stage of at least one nucleic acid biomarker obtained from a sample. When the methylation stage of nucleic acid isolated from a sample at each stage of bladder cancer is compared with the methylation stage of at least one nucleic acid obtained from a sample having no abnormality in the cell proliferation of bladder tissue, a certain stage of bladder cancer in the sample can be determined. The methylation stage may be hypermethylation.

In one embodiment of the present invention, nucleic acid can be methylated in the regulatory region of a gene. In another embodiment, since methylation begins from the outer boundary of the regulatory region of a gene and then spreads inward, detection of methylation at the outer boundary of the regulatory region enables early diagnosis of genes which are involved in cell transformation.

In still another embodiment of the present invention, the cell growth abnormality (dysplasia) of bladder tissue can be diagnosed by detecting the methylation of at least one nucleic acid of the following nucleic acids using a kit or a nucleic acid chip: CDX2 (NM_001265, caudal type homeobox transcription factor 2); CYP1B1 (NM_000104, cytochrome P450, family 1, subfamily B, polypeptide 1); VSX1 (NM_199425, visual system homeobox 1 homolog, CHX10-like (zebrafish)); HOXA11 (NM_005523, homeobox A11); T (NM_003181, T, brachyury homolog (mouse)); TBX5 (NM_080717, T-box 5); PENK (NM_006211, proenkephalin); and PAQR9 (NM_198504, progestin and adipoQ receptor family member IV); LHX2 (NM_004789) LIM Homeobox 2; SIM2 (U80456), single-minded homog 2 (Drosophila) gene and combination thereof.

The use of the diagnostic kit or nucleic acid chip of the present invention can determine the cell growth abnormality of bladder tissue in a sample. The method for determining the cell growth abnormality of bladder tissue comprises determining the methylation of at least one nucleic acid isolated from a sample. In the method, the methylation stage of at least one nucleic acid is compared with the methylation stage of a nucleic acid isolated from a sample having no cell growth abnormality (dysplasia).

The examples of said nucleic acid are follows: CDX2 (NM_001265, caudal type homeobox transcription factor 2); CYP1B1 (NM_000104, cytochrome P450, family 1, subfamily B, polypeptide 1); VSX1 (NM_199425, visual system homeobox 1 homolog, CHX10-like (zebrafish)); HOXA11 (NM_005523, homeobox A11); T (NM_003181, T, brachyury homolog (mouse)); TBX5 (NM_080717, T-box 5); PENK (NM_006211, proenkephalin); and PAQR9 (NM_198504, progestin and adipoQ receptor family member IV); LHX2 (NM_004789) LIM Homeobox 2; SIM2 (U80456), single-minded homog 2 (Drosophila) gene and combination thereof.

In still another embodiment of the present invention, cells capable of forming bladder cancer can be diagnosed at an early stage using the methylation gene marker. When genes confirmed to be methylated in cancer cells are methylated in cells which seem to be normal clinically or morphologically, the cells that seem to be normal are cells, the carcinogenesis of which is in progress. Thus, bladder cancer can be diagnosed at an early stage by detecting the methylation of bladder cancer-specific genes in the cells that seem to be normal.

The use of the methylation marker gene of the present invention enables detection of the cell growth abnormality (dysplasia progression) of bladder tissue in a sample. The method for detecting the cell growth abnormality (dysplasia progression) of bladder tissue comprises bringing at least one nucleic acid isolated from a sample into contact with an agent capable of determining the methylation status of the nucleic acid. The method comprises determining the methylation status of at least one region in at least one nucleic acid, and the methylation status of the nucleic acid differs from the methylation status of the same region in a nucleic acid isolated from a sample having no cell growth abnormality (dysplasia progression) of bladder tissue.

In still another embodiment of the present invention, transformed bladder cancer cells can be detected by examining the methylation of a marker gene using the above-described kit or nucleic acid chip.

In still another embodiment of the present invention, bladder cancer can be diagnosed by examining the methylation of a marker gene using the above-described kit or nucleic acid chip.

In still another embodiment of the present invention, the likelihood of progression to bladder cancer can be diagnosed by examining the methylation of a marker gene with the above-described kit or nucleic acid chip in a sample showing a normal phenotype. The sample may be solid or liquid tissue, cell, urine, serum or plasma.

In still another aspect, the present invention relates to a method for detecting the promoter methylation of a clinical sample-originated gene.

In the present invention, the method for measuring the promoter methylation of a clinical sample-originated gene may be selected from the group consisting of PCR, methylation specific PCR, real-time methylation specific PCR, PCR using a methylated DNA-specific binding protein, quantitative PCR, pyrosequencing and bisulfite sequencing, and the clinical sample is preferably a tissue, cell, blood or urine originated from patients suspected of cancer or subjects to be diagnosed.

In the present invention, the method for detecting the promoter methylation of the gene comprises the steps of: (a) isolating a sample DNA from a clinical sample; (b) amplifying the isolated DNA with primers capable of amplifying a fragment containing the promoter CpG island of a gene selected from the group consisting of CDX2, CYP1B1, VSX1, HOXA11, T, TBX5, PENK, PAQR9, LHX2 and SIM2; and (c) determining the promoter methylation of the DNA on the basis of whether the DNA has been amplified or not in step (b).

In another embodiment of the present invention, the likelihood of development of tissue to bladder cancer can be evaluated by examining the methylation frequency of a gene which is methylated specifically in bladder cancer and determining the methylation frequency of tissue having the likelihood of progression to bladder cancer.

As used herein, "cell conversion" refers to the change in characteristics of a cell from one form to another such as from normal to abnormal, non-tumorous to tumorous, undifferentiated to differentiated, stem cell to non-stem cell. Further, the conversion may be recognized by morphology of the cell, phenotype of the cell, biochemical characteristics and so on.

As used herein, the term "early diagnosis" of cancer refers to discovering the likelihood of cancer before metastasis. Preferably, it refers to discovering the likelihood of cancer before a morphological change in a sample tissue or cell is observed. Additionally, the term "early diagnosis" of transformation the high probability of a cell to undergo transformation in its early stages before the cell is morphologically designated as being transformed.

As used herein, the term "hypermethylation" refers to the methylation of CpG islands.

As used herein, the term "sample" or "biological sample" is referred to in its broadest sense, and includes any biological sample obtained from an individual, body fluid, cell line, tissue culture or other sources, according to the type of analysis that is to be performed. Methods of obtaining body fluid and tissue biopsy from mammals are generally widely known. A preferred source is bladder biopsy.

Screening for Methylation Regulated Biomarkers

The present invention is directed to a method of determining biomarker genes that are methylated when the cell or tissue is converted or changed from one type of cell to another. As used herein, "converted" cell refers to the change in characteristics of a cell or tissue from one form to another such as from normal to abnormal, non-tumorous to tumorous, undifferentiated to differentiated and so on.

In one Example of the present invention, urinary cells were isolated from the urine of normal persons and bladder cancer patients, and then genomic DNAs were isolated from the urinary cells. In order to obtain only methylated DNAs from the genomic DNAs, the genomic DNAs were allowed to react with McrBt binding to methylated DNA, and then methylated DNAs binding to the McrBt protein were isolated. The isolated methylated DNAs binding to the McrBt protein were amplified, and then the DNAs originated from the normal persons were labeled with Cy3, and the DNAs originated from the bladder cancer patients were labeled with Cy5. Then, the DNAs were hybridized to human CpG-island microarrays, and 10 genes showing the greatest difference in methylation degree between the normal persons and the bladder cancer patients were selected as biomarkers.

In the present invention, in order to further confirm whether the 10 biomarkers have been methylated, pyrosequencing was performed.

Specifically, total genomic DNA was isolated from the bladder cell lines RT-4, J82, HT1197 and HT1376 and treated with bisulfite. The genomic DNA converted with bisulfite was amplified. Then, the amplified PCR product was subjected to pyrosequencing in order to measure the methylation degree of the genes. As a result, it could be seen that the 10 biomarkers were all methylated.

Biomarker for Bladder Cancer

The present invention provides a biomarker for diagnosing bladder cancer.

Biomarkers for Bladder Cancer—Using Cancer Cells for Comparison with Normal Cells In one embodiment of the present invention, it is understood that "normal" cells are those that do not show any abnormal morphological or cytological changes. "Tumor" cells mean cancer cells. "Non-tumor" cells are those cells that were part of the diseased tissue but were not considered to be the tumor portion.

In one aspect, the present invention is based on the relationship between bladder cancer and the hypermethylation of the promoter or exon region of the following 10 genes: CDX2 (NM_001265, caudal type homeobox transcription factor 2); CYP1B1 (NM_000104, cytochrome P450, family 1, subfamily B, polypeptide 1); VSX1 (NM_199425, visual system homeobox 1 homolog, CHX10-like (zebrafish)); HOXA11 (NM_005523, homeobox A11); T (NM_003181, T, brachyury homolog (mouse)); TBX5 (NM_080717, T-box 5); PENK (NM_006211, proenkephalin); and PAQR9 (NM_198504, progestin and adipoQ receptor family member IV); LHX2 (NM_004789)—LIM Homeobox 2; and SIM2 (U80456)—single-minded homolog 2 (Drosophila); gene.

With other applications of the diagnostic kit or nucleic acid chip of the present invention, the invention can diagnose a cellular proliferative disorder of bladder tissue in a subject by determining the state of methylation of one or more nucleic acids isolated from the subject, wherein the state of methylation of one or more nucleic acids as compared with the state of methylation of one or more nucleic acids from a subject not having the cellular proliferative disorder of bladder tissue is indicative of a cellular proliferative disorder of bladder tissue in the subject. A preferred nucleic acid is a CpG-containing nucleic acid, such as a CpG island.

With other applications of the diagnostic kit or nucleic acid chip of the present invention, the cell growth abnormality of bladder tissue in a subject can be diagnosed comprising determining the methylation of one or more nucleic acids isolated from the subject. Said nucleic acid is preferably encoding the followings: CDX2 (NM_001265, caudal type homeobox transcription factor 2); CYP1B1 (NM_000104, cytochrome P450, family 1, subfamily B, polypeptide 1); VSX1 (NM_199425, visual system homeobox 1 homolog, CHX10-like (zebrafish)); HOXA11 (NM_005523, homeobox A11); T (NM_003181, T, brachyury homolog (mouse)); TBX5 (NM_080717, T-box 5); PENK (NM_006211, proenkephalin); and PAQR9 (NM_198504, progestin and adipoQ receptor family member IV); LHX2 (NM_004789)—LIM Homeobox 2; and SIM2 (U80456)—single-minded homolog 2 (Drosophila); gene and combinations thereof. The state of methylation of one or more nucleic acids as compared with the state of methylation of said nucleic acid from a subject not having a predisposition to the cellular proliferative disorder of bladder tissue is indicative of a cell proliferative disorder of bladder tissue in the subject.

As used herein, "predisposition" refers to an increased likelihood that an individual will have a disorder. Although a subject with a predisposition does not yet have the disorder, there exists an increased propensity to the disease.

Another embodiment of the invention provides a method for diagnosing a cellular proliferative disorder of bladder tissue in a subject comprising contacting a nucleic acid-containing specimen from the subject with an agent that provides a determination of the methylation state of nucleic acids in the specimen, and identifying the methylation state of at least one region of at least one nucleic acid, wherein the methylation state of at least one region of at least one nucleic acid that is different from the methylation state of the same region of the same nucleic acid in a subject not having the cellular proliferative disorder is indicative of a cellular proliferative disorder of bladder tissue in the subject.

The inventive method includes determining the state of methylation of one or more regions of one or more nucleic acids isolated from the subject. The phrases "nucleic acid" or "nucleic acid sequence" as used herein refer to an oligonucleotide, nucleotide, polynucleotide, or to a fragment of any of these, to DNA or RNA of genomic or synthetic origin which may be single-stranded or double-stranded, to DNA or RNA of genomic or synthetic origin which may represent a sense or antisense strand, peptide nucleic acid (PNA), or to any DNAlike or RNA-like material of natural or synthetic origin. As will be understood by those of skill in the art, when the nucleic acid is RNA, the deoxynucleotides A, G, C, and T are replaced by ribonucleotides A, G, C, and U, respectively.

The nucleic acid of interest can be any nucleic acid where it is desirable to detect the presence of a differentially methylated CpG island. The CpG island is a CpG rich region of a nucleic acid sequence.

Methylation

Any nucleic acid sample, in purified or nonpurified form, can be utilized in accordance with the present invention, provided it contains or is suspected of containing, a nucleic acid sequence containing a target locus (e.g., CpG-containing nucleic acid). One nucleic acid region capable of being differentially methylated is a CpG island, a sequence of nucleic acid with an increased density relative to other nucleic acid regions of the dinucleotide CpG. The CpG doublet occurs in vertebrate DNA at only about 20% of the frequency that would be expected from the proportion of G*C base pairs. In certain regions, the density of CpG doublets reaches the predicted value; it is increased by ten fold relative to the rest of the genome. CpG islands have an average G*C content of about 60%, and general DNA have an average G*C contents of about 40%. The islands take the form of stretches of DNA typically about one to two kilobases long. There are about 45,000 such islands in the human genome.

In many genes, the CpG islands begin just upstream of a promoter and extend downstream into the transcribed region. Methylation of a CpG island at a promoter usually prevents expression of the gene. The islands can also surround the 5' region of the coding region of the gene as well as the 3' region of the coding region. Thus, CpG islands can be found in multiple regions of a nucleic acid sequence including upstream of coding sequences in a regulatory region including a promoter region, in the coding regions (e.g., exons), in downstream of coding regions, for example, enhancer regions, and in introns.

In general, the CpG-containing nucleic acid is DNA. However, invention methods may employ, for example, samples that contain DNA, or DNA and RNA, including messenger RNA, wherein DNA or RNA may be single stranded or double stranded, or a DNA-RNA hybrid may be included in the sample.

A mixture of nucleic acids may also be employed. The specific nucleic acid sequence to be detected may be a fraction of a larger molecule or can be present initially as a discrete molecule, so that the specific sequence constitutes the entire nucleic acid. It is not necessary that the nucleic acid sequence is present initially in a pure form, the nucleic acid may be a minor fraction of a complex mixture, such as contained in whole human DNA. The nucleic acid-containing sample used for determination of the state of methylation of nucleic acids contained in the sample or detection of methylated CpG islands may be extracted by a variety of techniques such as that described by Sambrook, et al. (Molecular Cloning: A Laboratory Manual, Cold Spring Harbor, N.Y., 1989; incorporated in its entirety herein by reference).

A nucleic acid can contain a regulatory region which is a region of DNA that encodes information or controls transcription of the nucleic acid. Regulatory regions include at least one promoter. A "promoter" is a minimal sequence sufficient to direct transcription, to render promoter-dependent gene expression controllable for cell-type specific, tissue-specific, or inducible by external signals or agents. Promoters may be located in the 5' or 3' regions of the gene. Promoter regions, in whole or in part, of a number of nucleic acids can be examined for sites of CpG-island methylation.

Moreover, it is generally recognized that methylation of the target gene promoter proceeds naturally from the outer boundary inward. Therefore, early stage of cell conversion can be detected by assaying for methylation in these outer areas of the promoter region.

Nucleic acids isolated from a subject are obtained in a biological specimen from the subject. If it is desired to detect bladder cancer or stages of bladder cancer progression, the nucleic acid may be isolated from bladder tissue by scraping or taking a biopsy. These specimens may be obtained by various medical procedures known to those of skill in the art.

In one aspect of the invention, the state of methylation in nucleic acids of the sample obtained from a subject is hypermethylation compared with the same regions of the nucleic acid in a subject not having the cellular proliferative disorder of bladder tissue. Hypermethylation, as used herein, is the presence of methylated alleles in one or more nucleic acids. Nucleic acids from a subject not having a cellular proliferative disorder of bladder tissues contain no detectable methylated alleles when the same nucleic acids are examined.

Sample

The present invention describes early diagnosis of bladder cancer and utilizes the methylation of bladder cancer-specific genes. The methylation of bladder cancer-specific genes also occurred in tissue near tumor sites. Therefore, in the method for early diagnosis of bladder cancer, the methylation of bladder cancer-specific genes can be detected by examining all samples including liquid or solid tissue. The samples include, but are not limited to, tissue, cell, urine, serum or plasma.

Individual Genes and Panel

It is understood that the present invention may be practiced using each gene separately as a diagnostic or prognostic marker, or a few marker genes combined into a panel display format so that several marker genes may be detected to increase reliability and efficiency. Further, any of the genes identified in the present application may be used individually or as a set of genes in any combination with any of the other genes that are recited in the application. Also, genes may be ranked and weighted according to their importance together with the number of genes that are methylated, and a level of likelihood of development to cancer can be assigned. Such algorithms are within the scope of the present invention.

Methylation Detection Methods

Methylation Specific PCR

When genomic DNA is treated with bisulfite, the methylated cytosine in the 5'-CpG'-3 region remains without changes, and unmethylated cytosine is changed to uracil. Thus, for a base sequence modified by bisulfite treatment, PCR primers corresponding to regions in which a 5'-CpG-3' base sequence is present were constructed. Herein, two kinds of primers corresponding to the methylated case and the unmethylated case were constructed. When genomic DNA is modified with bisulfite and then subjected to PCR using the two kinds of primers, in the case in which the DNA is methylated, a PCR product is made from the DNA in which the primers corresponding to the methylated base sequence are used. In contrast, in the case in which the gene is unmethylated, a PCR product is made from the DNA in which the primers corresponding to the unmethylated base sequence are used. The methylation of DNA can be qualitatively analyzed using agarose gel electrophoresis.

Real-Time Methylation-Specific PCR

Real-time methylation-specific PCR is a real-time measurement method modified from methylation-specific PCR, and comprises treating genomic DNA with bisulfite, designing PCR primers corresponding to the methylated case and performing real-time PCR using the primers. Herein, methods of detecting methylation include two methods: a method of performing detection using a TanMan probe complementary to the amplified base sequence, and a method of performing detection using Sybergreen. Thus, real-time methylation-specific PCR selectively quantitatively analyze only DNA. Herein, a standard curve was prepared using an in vitro methylated DNA sample, and for standardization, a gene having no 5'-CpG-3' sequence in the base sequence was also amplified as a negative control group and was quantitatively analyzed for the methylation degree.

Pyrosequencing

Pyrosequencing is a real-time sequencing method modified from a bisulfite sequencing method. In the same manner as bisulfite sequencing, genomic DNA was modified by bisulfite treatment, and then primers corresponding to a region having no 5'-CpG-3' base sequence were constructed. After the genomic DNA had been treated with bisulfite, it was amplified with the PCR primers, and then subjected to real-time sequence analysis using sequencing primers. The amounts of cytosine and thymine in the 5'-CpG-3' region were quantitatively analyzed, and the methylation degree was expressed as a methylation index.

PCR or Quantitative PCR Using Methylated DNA-Specific Binding Protein and DNA Chip In a PCR or DNA chip method using a methylated DNA-specific binding protein, when a protein binding specifically only to methylated DNA is mixed with DNA, the protein binds specifically only to methylated DNA, and thus only methylated DNA can be isolated. In the present invention, genomic DNA was mixed with a methylated DNA-specific binding protein, and then only methylated DNA was selectively isolated. The isolated DNA was amplified using PCR primers corresponding to the promoter region thereof, and then the methylation of the DNA was measured by agarose gel electrophoresis.

In addition, the methylation of DNA can also be measured by a quantitative PCR method. Specifically, methylated DNA isolated using a methylated DNA-specific binding protein can be labeled with a fluorescent dye and hybridized to a DNA chip in which complementary probes are integrated, thus measuring the methylation of the DNA. Herein, the methylated DNA-specific binding protein is not limited to McrBt.

Detection of Differential Methylation-Methylation Sensitive Restriction Endonuclease Detection of differential methylation can be accomplished by contacting a nucleic acid sample with a methylation sensitive restriction endonuclease that cleaves only unmethylated CpG sites under conditions and for a time to allow cleavage of unmethylated nucleic acid.

In a separate reaction, the sample is further contacted with an isoschizomer of the methylation sensitive restriction endonuclease that cleaves both methylated and unmethylated CpG-sites under conditions and for a time to allow cleavage of methylated nucleic acid.

Specific primers are added to the nucleic acid sample under conditions and for a time to allow nucleic acid amplification to occur by conventional methods. The presence of amplified product in the sample digested with methylation sensitive restriction endonuclease but absence of an amplified product in sample digested with an isoschizomer of the methylation sensitive restriction enzyme endonuclease that cleaves both methylated and unmethylated CpG-sites indicates that methylation has occurred at the nucleic acid region being assayed. However, lack of amplified product in the sample digested with methylation sensitive restriction endonuclease together with lack of an amplified product in the sample digested with an isoschizomer of the methylation sensitive restriction enzyme endonuclease that cleaves both methylated and unmethylated CpG-sites indicates that methylation has not occurred at the nucleic acid region being assayed.

As used herein, a "methylation sensitive restriction endonuclease" is a restriction endonuclease that includes CG as part of its recognition site and has altered activity when the C is methylated as compared to when the C is not methylated (e.g., Sma I). Non-limiting examples of methylation sensitive restriction endonucleases include MspI, HpaII, BssHII, BstUI and NotI. Such enzymes can be used alone or in combination. Other methylation sensitive restriction endonucleases such as SacII and EagI may be applied to the present invention, but are not limited to these enzymes.

An "isoschizomer" of a methylation sensitive restriction endonuclease is a restriction endonuclease that recognizes the same recognition site as a methylation sensitive restriction endonuclease but cleaves both methylated CGs and unmethylated CGs, such as for example, MspI.

Primers of the invention are designed to be "substantially" complementary to each strand of the locus to be amplified and include the appropriate G or C nucleotides as discussed above. This means that the primers must be sufficiently complementary to hybridize with their respective strands under conditions that allow the agent for polymerization to perform. Primers of the invention are employed in the amplification process, which is an enzymatic chain reaction that produces exponentially increasing quantities of target locus relative to the number of reaction steps involved (e.g., polymerase chain reaction (PCR)). Typically, one primer is complementary to the negative (−) strand of the locus (antisense primer) and the other is complementary to the positive (+) strand (sense primer) Annealing the primers to denatured nucleic acid followed by extension with an enzyme, such as the large fragment of DNA Polymerase I (Klenow) and nucleotides, results in newly synthesized + and − strands containing the target locus sequence. Because these newly synthesized sequences are also templates, repeated cycles of denaturing, primer annealing, and extension results in exponential production of the region (i.e., the target locus sequence) defined by the primer. The product of the chain reaction is a discrete nucleic acid duplex with termini corresponding to the ends of the specific primers employed.

Preferably, the method of amplifying is by PCR, as described herein and as is commonly used by those of ordinary skill in the art. However, alternative methods of amplification have been described and can also be employed such as real time PCR or linear amplification using isothermal enzyme. Multiplex amplification reactions may also be used.

Detection of Differential Methylation-Bifulfite Sequencing Method

Another method for detecting a methylated CpG-containing nucleic acid includes contacting a nucleic acid-containing specimen with an agent that modifies unmethylated cytosine, amplifying the CpG-containing nucleic acid in the specimen by means of CpG-specific oligonucleotide primers, wherein the oligonucleotide primers distinguish between modified methylated and non-methylated nucleic acid and detecting the methylated nucleic acid. The amplification step is optional and although desirable, is not essential. The method relies on the PCR reaction itself to distinguish between modified (e.g., chemically modified) methylated and unmethylated DNA. Such methods are described in U.S. Pat. No. 5,786,146, the contents of which are incorporated herein in their entirety especially as they relate to the bisulfate sequencing method for detection of methylated nucleic acid.

Substrates

Once the target nucleic acid region is amplified, the nucleic acid can be hybridized to a known gene probe immobilized on a solid support to detect the presence of the nucleic acid sequence.

As used herein, "substrate," when used in reference to a substance, structure, surface or material, means a composition comprising a nonbiological, synthetic, nonliving, planar, spherical or flat surface that is not heretofore known to comprise a specific binding, hybridization or catalytic recognition site or a plurality of different recognition sites or a number of different recognition sites which exceeds the number of different molecular species comprising the surface, structure or material. The substrate may include, for example and without limitation, semiconductors, synthetic (organic) metals, synthetic semiconductors, insulators and dopants; metals, alloys, elements, compounds and minerals; synthetic, cleaved, etched, lithographed, printed, machined and microfabricated slides, devices, structures and surfaces; industrial polymers, plastics, membranes; silicon, silicates, glass, metals and ceramics; wood, paper, cardboard, cotton, wool, cloth, woven and nonwoven fibers, materials and fabrics.

Several types of membranes are known to one of skill in the art for adhesion of nucleic acid sequences. Specific non-limiting examples of these membranes include nitrocellulose or other membranes used for detection of gene expression such as polyvinylchloride, diazotized paper and other commercially available membranes such as GENESCREEN™, ZETAPROBE™ (Biorad), and NYTRAN™. Beads, glass, wafer and metal substrates are included. Methods for attaching nucleic acids to these objects are well known to one of skill in the art. Alternatively, screening can be done in liquid phase.

Hybridization Conditions

In nucleic acid hybridization reactions, the conditions used to achieve a particular level of stringency will vary, depending on the nature of the nucleic acids being hybridized. For example, the length, degree of homology, nucleotide sequence composition (e.g., GC/AT content), and nucleic acid type (e.g., RNA, DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically. In general, conditions of high stringency are used for the hybridization of the probe of interest.

Label

The probe of interest can be detectably labeled, for example, with a radioisotope, a fluorescent compound, a bioluminescent compound, a chemiluminescent compound, a metal chelator, or an enzyme. Those of ordinary skill in the art will know of other suitable labels for binding to the probe, or will be able to ascertain such, using routine experimentation.

Kit

In accordance with the present invention, there is provided a kit useful for the detection of a cellular proliferative disorder in a subject. Kits according to the present invention include a carrier means compartmentalized to receive a sample therein, one or more containers comprising a first container containing a reagent which sensitively cleaves unmethylated cytosine, a second container containing primers for amplification of a CpG-containing nucleic acid, and a third container containing a means to detect the presence of cleaved or uncleaved nucleic acid. Primers contemplated for use in accordance with the invention include those set forth in SEQ ID NOS: 1-20, and any functional combination and fragments thereof. Functional combination or fragment refers to its ability to be used as a primer to detect whether methylation has occurred on the region of the genome sought to be detected.

Carrier means are suited for containing one or more container means such as vials, tubes, and the like, each of the container means comprising one of the separate elements to be used in the method. In view of the description provided herein of invention methods, those of skill in the art can readily determine the apportionment of the necessary reagents among the container means. For example, one of the container means can comprise a container containing methylation sensitive restriction endonuclease. One or more container means can also be included comprising a primer complementary to the nucleic acid locus of interest. In addition, one or more container means can also be included containing an isoschizomer of the methylation sensitive restriction enzyme.

EXAMPLES

Hereinafter, the present invention will be described in further detail with reference to examples. It is to be understood, however, that these examples are for illustrative purposes only and are not to be construed to limit the scope of the present invention.

Example 1

Discovery of Bladder Cancer-Specific Methylated Genes

In order to screen biomarkers which are methylated specifically in bladder cancer, about 20 ml of the urine of each of 10 bladder cancer patients and 10 normal persons was centrifuged in a centrifuge (Hanil Science Industrial Co., Ltd., Korea) at 4,200×g for 10 minutes to isolate urinary cells. The supernatant was discarded, and the cell precipitate was washed twice with 5 ml of PBS. Genomic DNA was isolated from the cell precipitate using the QIAamp DNA Mini kit (QIAGEN, USA). 500 ng of the isolated genomic DNA was sonicated (Vibra Cell, SONICS), thus constructing about 200-300-bp-genomic DNA fragments.

To obtain only methylated DNA from the genomic DNA, a methyl binding domain (MBD) known to bind to methylated DNA (Fraga et al., *Nucleic Acid Res.*, 31:1765-1774, 2003) was used. Specifically, 2 μg of 6×His-tagged MBD was pre-incubated with 500 ng of the genomic DNA of *E. coli* JM110 (No. 2638, Biological Resource Center, Korea Research Institute of Bioscience & Biotechnology), and then bound to Ni-NTA magnetic beads (Qiagen, USA). 500 ng of the sonicated genomic DNA isolated from the urinary cells of the normal persons and the bladder cancer patients was allowed to react with the beads in the presence of binding buffer solution (10 mM Tris-HCl (pH 7.5), 50 mM NaCl, 1 mM EDTA, 1 mM DTT, 3 mM $MgCl_2$, 0.1% Triton-X100, 5% glycerol, 25 mg/ml BSA) at 4° C. for 20 minutes. Then, the beads were washed three times with 500 μl of a binding buffer solution containing 700 mM NaCl, and then methylated DNA bound to the MBD was isolated using the QiaQuick PCR purification kit (QIAGEN, USA).

Then, the methylated DNAs bound to the MBD were amplified using a genomic DNA amplification kit (Sigma, USA, Cat. No. WGA2), and 4 μg of the amplified DNAs were labeled with Cy3 for the normal person-originated DNA and with Cy5 for the bladder cancer patient-originated DNA using the BioPrime Total Genomic Labeling system I (Invitrogen Corp., USA). The DNA of the normal persons and the DNA of the bladder patients were mixed with each other, and then hybridized to 244K human CpG microarrays (Agilent, USA) (FIG. 1). After the hybridization, the DNA mixture was subjected to a series of washing processes, and then scanned using an Agilent scanner. The calculation of signal values from the microarray images was performed by calculating the relative difference in signal strength between the normal person sample and the bladder cancer patient sample using Feature Extraction program v. 9.5.3.1 (Agilent).

In order to select unmethylated spots from the normal sample, the whole Cy3 signal values were averaged, and then spots having a signal value of less than 10% of the averaged value were regarded as those unmethylated in the samples of the normal persons. As a result, 41,674 spots having a Cy3 signal value of less than 65 were selected.

In order to select the methylated spots in the samples of the bladder cancer patients from among the 41,674 spots, spots having a Cy5 signal value of more than 130 were regarded as the methylated spots in bladder cancer. As a result, 631 spots having a Cy5 signal value of more than 130 were selected. From these spots, 227 genes corresponding to the promoter region were secured as bladder cancer-specific methylated genes.

From the genes, 10 genes (CDX2, CYP1B1, VSX16, HOXA11, T, TBX5, PENK, PAQR9, LHX2, and SIM2) showing the greatest relative difference between methylation degree of the normal persons and that of the bladder cancer patients were selected, and the presence of CpG islands in the promoter region of the 10 genes was confirmed using MethPrimer. The 10 genes were secured as methylation biomarkers for diagnosis of bladder cancer. The list of the 10 genes and the relative methylation degree thereof in the urinary cells of the bladder patients relative to those of the normal persons are shown in Table 1 below.

TABLE 1

10 methylation biomarkers for diagnosis of bladder cancer

| Biomarker for bladder cancer | GenBank No. | Description | Relative methylation[a] |
|---|---|---|---|
| CDX2 | NM_001265 | caudal type homeobox transcription factor 2 | 11.0 |

TABLE 1-continued 10 methylation biomarkers for diagnosis of bladder cancer

| Biomarker for bladder cancer | GenBank No. | Description | Relative methylation[a] |
|---|---|---|---|
| CYP1B1 | NM_000104 | cytochrome P450, family 1, subfamily B, polypeptide 1 | 14.6 |
| VSX1 | NM_199425 | visual system homeobox 1 homolog, CHX10-like (zebrafish) | 33.4 |
| HOXA11 | NM_005523 | homeobox A11 | 14.2 |
| T | NM_003181 | T, brachyury homolog (mouse) | 51.4 |
| TBX5 | NM_080717 | T-box 5 | 18.7 |
| PENK | NM_006211 | Proenkephalin | 12.7 |
| PAQR9 | NM_198504 | progestin and adipoQ receptor family member IX | 4.1 |
| LHX2 | NM_004789 | LIM Homeobox 2 | 5.8 |
| SIM2 | U80456 | Single-minded homolog 2 (Drosophila) | 9.5 |

[a]Relative methylation degree between the normal sample and the bladder patient sample, calculated by dividing the average signal (Cy5) value in the bladder cancer patient sample in CpG microarrays by the average signal (Cy5) value in the normal person sample.

Example 2

Measurement of Methylation of Biomarker Genes in Cancer Cell Lines

In order to further determine the methylation status of the 10 genes, bisulfite sequencing for each promoter was performed.

In order to modify unmethylated cytosine to uracil using bisulfite, total genomic DNA was isolated from the bladder cancer cell lines RT-4 (Korean Cell Line Bank (KCLB 30002), J82 (KCLB 30001), HT1197 (KCLB 21473) and HT1376 (KCLB 21472), and 200 ng of the genomic DNA was treated with bisulfite using the EZ DNA methylation-gold kit (Zymo Research, USA). When DNA is treated with bisulfite, unmethylated cytosine is modified to uracil, and the methylated cytosine remains without changes. The DNA treated with bisulfite was eluted in 20 μl of sterile distilled water and subjected to pyrosequencing.

PCR and sequencing primers for performing pyrosequencing for the 10 genes were designed using the PSQ assay design program (Biotage, USA). The PCR and sequencing primers for measuring the methylation of each gene are shown in Tables 2 and 3 below.

TABLE 2

Primers and conditions

| Gene | Primer | Sequence (5'→3') | SEQ ID NO: | CpG position[a] | Amplicon size |
|---|---|---|---|---|---|
| CDX2 | forward | TGGTGTTTGTGTTATTATTAATAG | 1 | -138, -129, -121, -118 | 129 bp |
| | reverse | Biotin-CACCTCCTTCCCACTAAACTA | 2 | | |
| CYP1B1 | forward | GTAAGGGTATGGGAATTGA | 3 | +73, +83, +105 | 90 bp |
| | reverse | Biotin-CCCTTAAAAACCTAACAAAATC | 4 | | |

TABLE 2 -continued

Primers and conditions

| Gene | Primer | Sequence (5'→3') | SEQ ID NO: | CpG position[a] | Amplicon size |
|---|---|---|---|---|---|
| VSX1 | forward | GGAGTGGGATTGAGGAGATTT | 5 | -1121, -1114, | 89 bp |
|  | reverse | Biotin-AAACCCAACCAACCCTCAT | 6 | -1104, 1100 |  |
| HOX411 | forward | AGTAAGTTTATGGGAGGGGATT | 7 | -415, 405, | 243 bp |
|  | reverse | Biotin-CCCCCATACAACATACTTATACTCA | 8 | -388 |  |
| T | forward | GGAGGAATGTTATTGTTTAAAGAGAT | 9 | -95, -89, | 326 bp |
|  | reverse | Biotin-CAACCCCTTCTAAAAAATATCC | 10 | -76, -71, -69 |  |
| TBX5 | forward | GGGTTTGGAGTTAGGTTATG | 11 | -645, -643, | 95 bp |
|  | reverse | Biotin-AAATCTAAACTTACCCCAACT | 12 | -628, -621 |  |
| PENK | forward | ATATTTTATTGTATGGGTTTTTTAATAG | 13 | -150, -148, | 322 bp |
|  | reverse | Biotin-ACAACCTCAACAAAAAATC | 14 | -139, -135 -133, | 54 bp |
| PAQR9 | forward | Biotin-AGATAGGGGATAATTTTAT | 15 | -480, -475, | 54 bp |
|  | reverse | CCTCCCAAACTAAAATTT | 16 | -471, -469 |  |
| LHX2 | forward | GTAGAAGGGAAATAAGGTTGAAA | 17 | +5093, +5102, | 233 bp |
|  | reverse | Biotin-ACTAAAACCCCAATACTCCCA | 18 | +5113, +5125, +5127 |  |
| SIM2 | forward | Biotin-GTGGATTTAGATTAGGATTTTGT | 19 | -6747, -6744, | 205 bp |
|  | reverse | CACCCTCCCCAAATTCTT | 20 | -6743 |  |

[a]distances (nucleotides) from the transcription initiation site (+1): the positions of CpG regions on the genomic DNA used in the measurement of methylation

TABLE 3

Sequences of sequencing primers for methylation marker genes

| Gene | Sequence (5' --> 3') | SEQ ID NO: |
|---|---|---|
| CDX2 | ATT AAT AGA GTT TTG TAA ATA T | 21 |
| CYP1B1 | AAG GGT ATG GGA ATT G | 22 |
| VSX1 | TTT GGG ATT GGG AAG | 23 |
| HOXA11 | TAG TTT AGG GTA TTT TTT ATT TAT | 24 |
| T | GTG AAA GTA ATG ATA TAG TAG AAA | 25 |
| TBX5 | TTT GGG GGT TGG GGA | 26 |
| PENK | GGG TGT TTTAGG TAG TT | 27 |
| PAQR9 | CCT CCC AAA CTA AAA TTT C | 28 |
| LHX2 | TGG GGG TAG AGG AGA | 29 |
| SIM2 | CCT CCC CAA ATT CTT C | 30 |

20 ng of the genomic DNA modified with bisulfite was amplified by PCR. In the PCR amplification, a PCR reaction solution (20 ng of the genomic DNA modified with bisulfite, 5 µl of 10×PCR buffer (Enzynomics, Korea), 5 units of Taq polymerase (Enzynomics, Korea), 4 µl of 2.5 mM dNTP (Solgent, Korea), and 2 µl (10 pmole/µl) of PCR primers) was used, and the PCR reaction was performed in the following conditions: predenaturation at 95° C. for 5 min, and then 45 cycles of denaturation at 95° C. for 40 sec, annealing at 60° C. for 45 sec and extension at 72° C. for 40 sec, followed by final extension at 72 r for 5 min. The amplification of the PCR product was confirmed by electrophoresis on 2.0% agarose gel.

The amplified PCR product was treated with PyroGold reagents (Biotage, USA), and then subjected to pyrosequencing using the PSQ96MA system (Biotage, USA). After the pyrosequencing, the methylation degree of the DNA was measured by calculating the methylation index. The methylation index was calculated by determining the average rate of cytosine binding to each CpG island.

Figure 2:
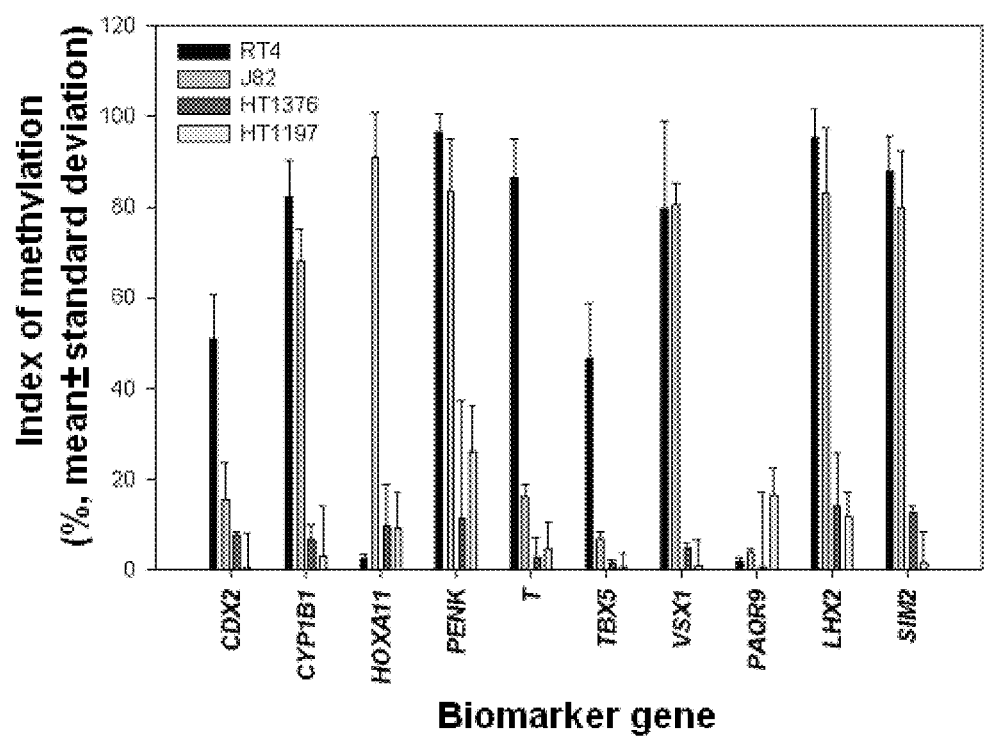
FIG. 2 quantitatively shows the methylation degree obtained through pyrosequencing of 10 methylation biomarkers in bladder cancer cell lines.
Figure 3A:
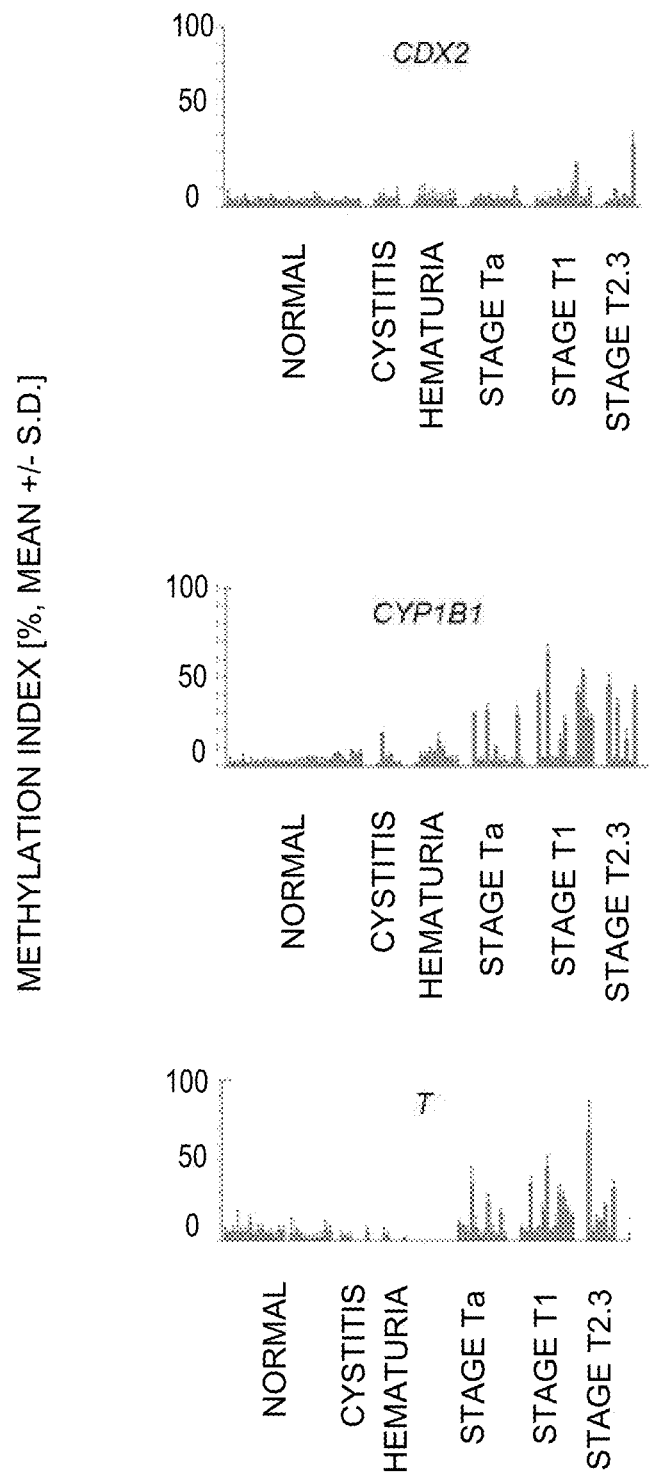
FIG. 3(A) shows measurement results for the methylation indexes of the CDX2, the CYP1B1 and the T biomarker genes in clinical samples.
Figure 3B:
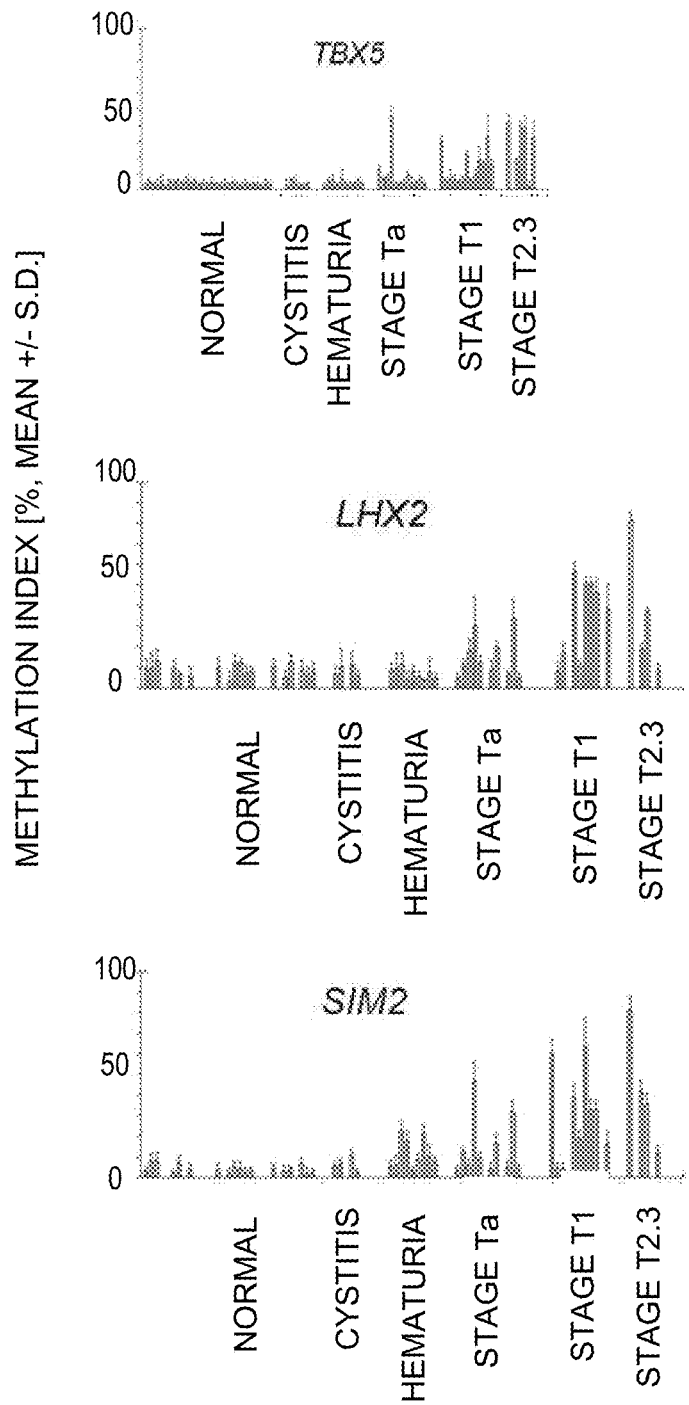
FIG. 3(B) shows measurement results for the methylation indexes of the TBX5, the LHX2 and the SIM2 biomarker genes in clinical samples.
Figure 3C:
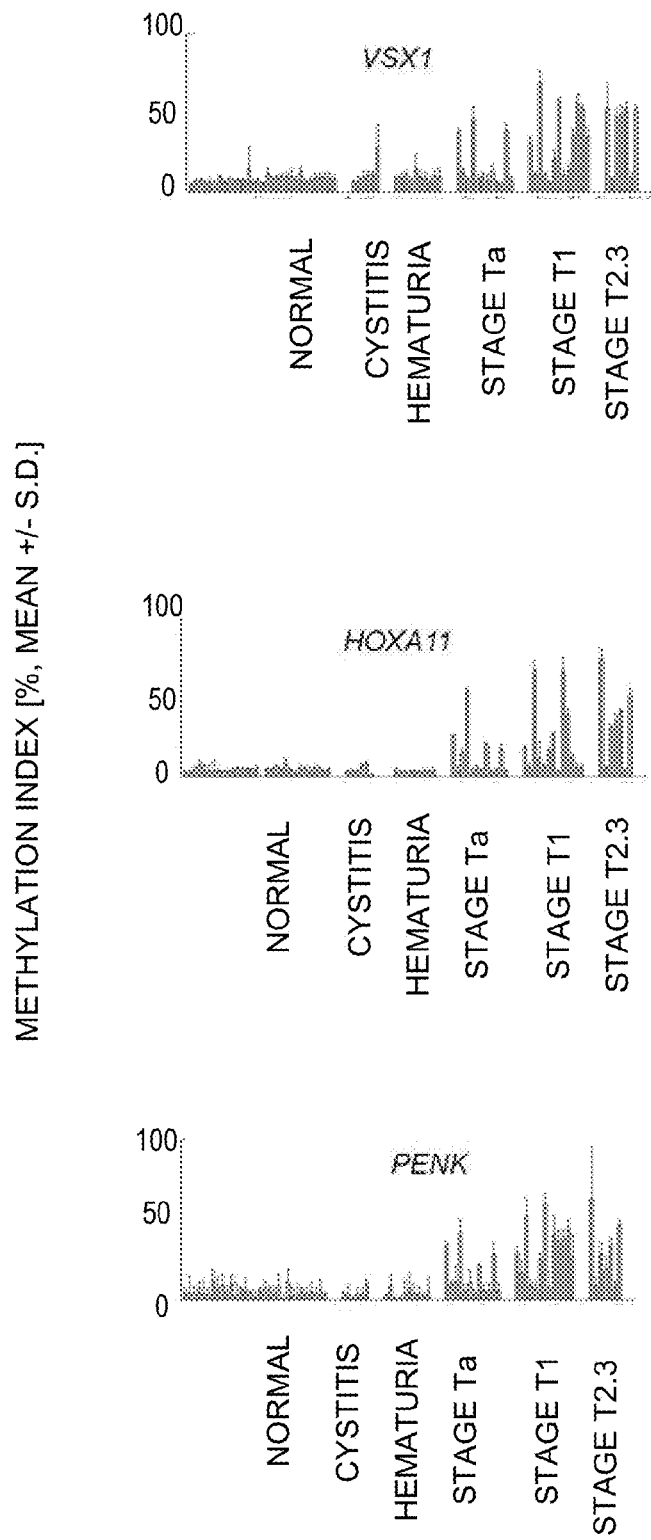
FIG. 3(C) shows measurement results for the methylation indexes of the VSX1, the HOXA11 and the PENK biomarker genes in clinical samples.
Figure 3D:
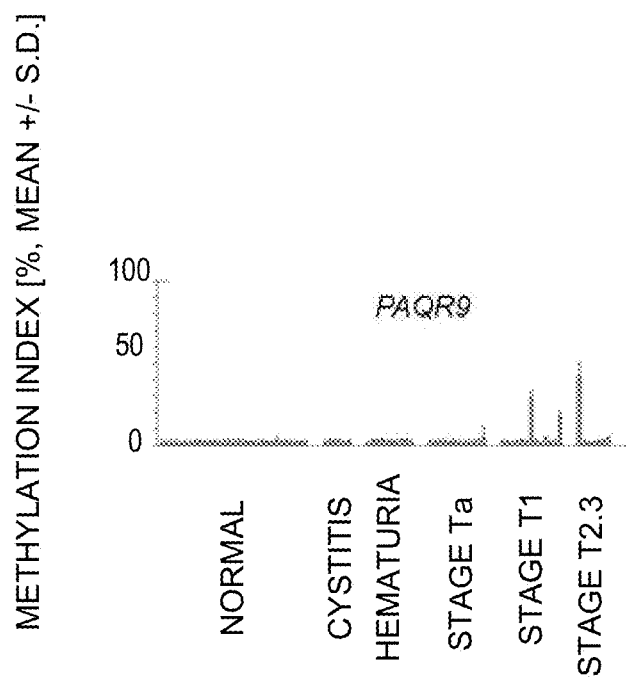
FIG. 3(D) shows measurement results for the methylation indexes of the PAQR9 biomarker genes in clinical samples.
Figure 4A:
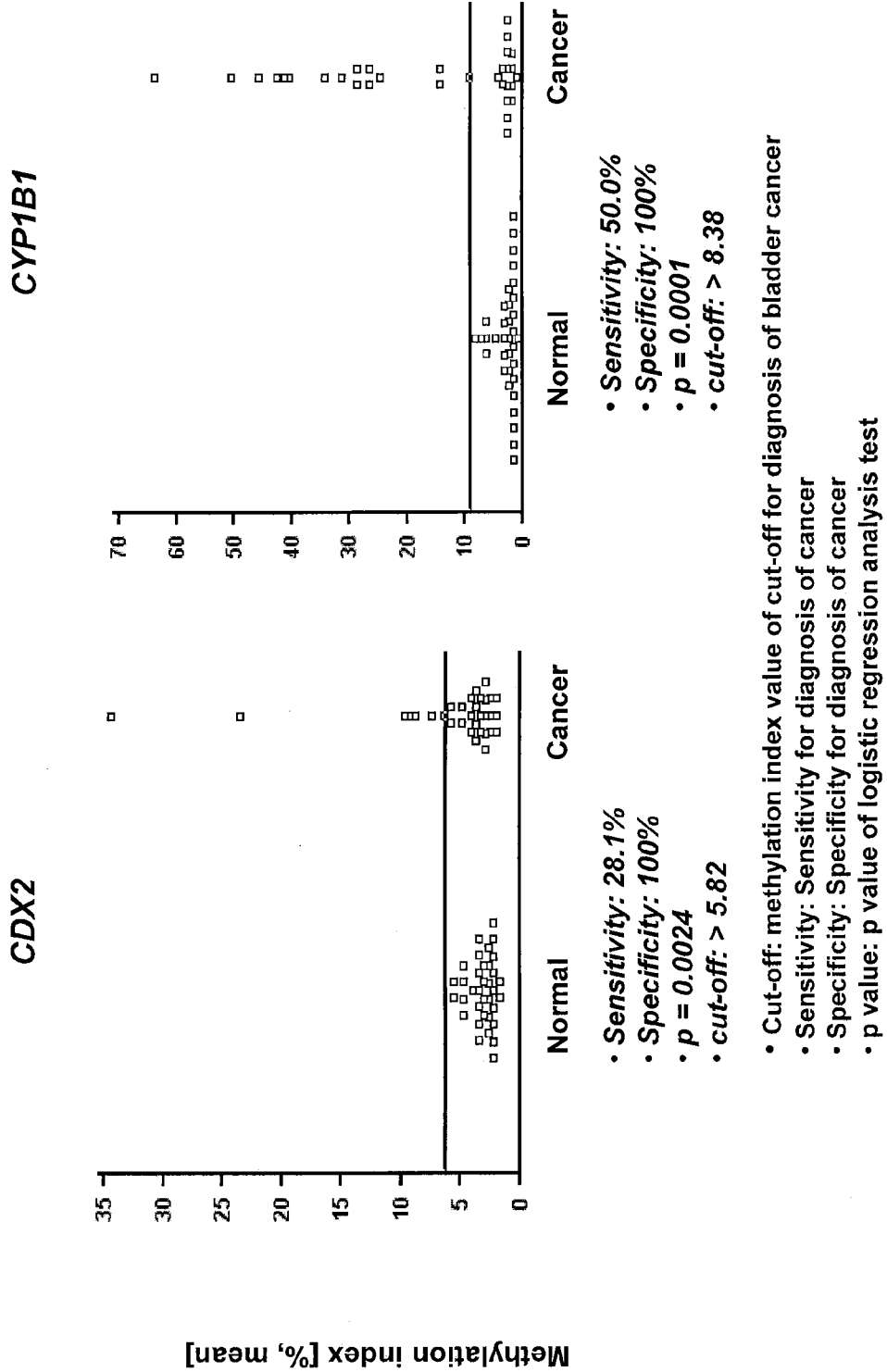
FIG. 4a shows the results of receiver operating characteristic (ROC) curve analysis conducted to measure the sensitivity and specificity of the CDX2 and the CYP1BI methylation biomarkers for diagnosis of bladder cancer.
Figure 4B:
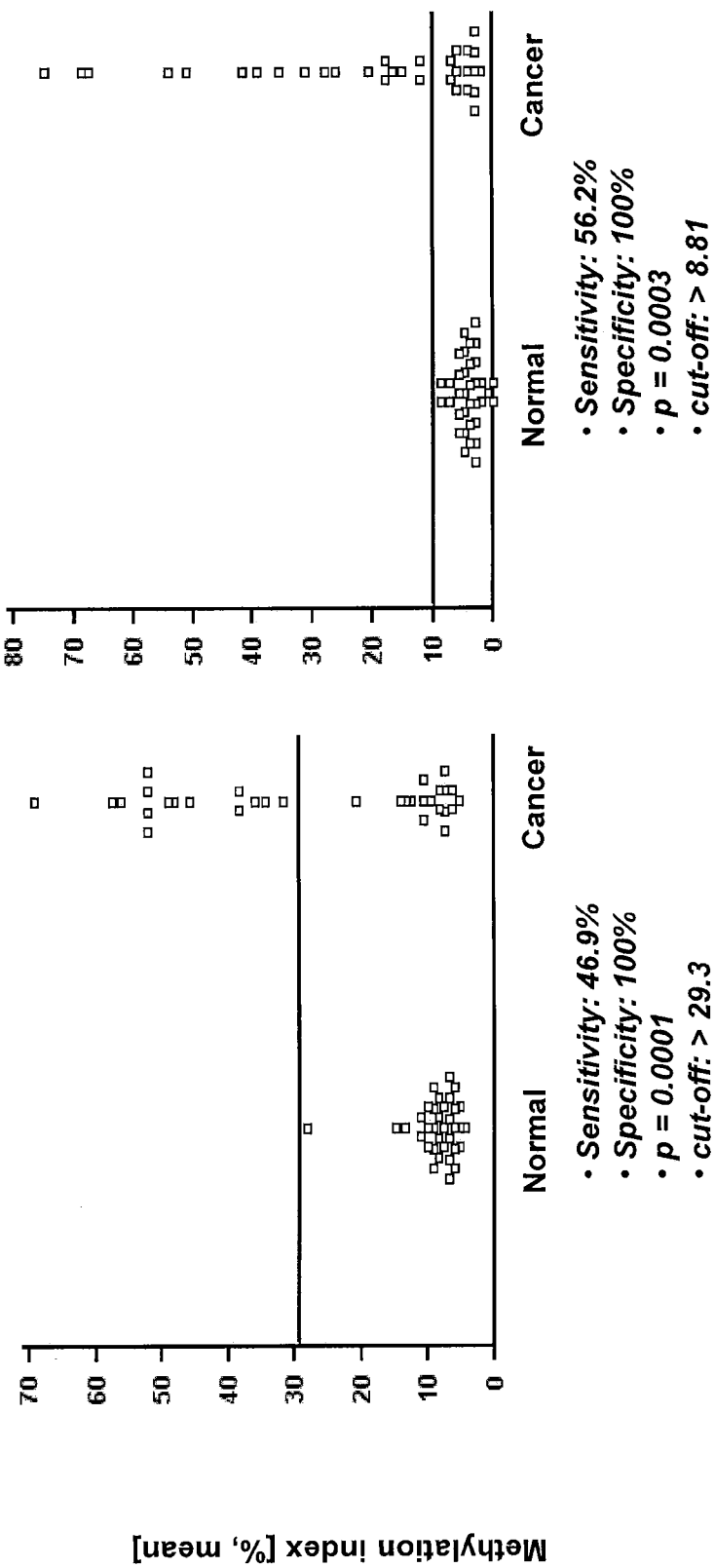
FIG. 4b shows the results of receiver operating characteristic (ROC) curve analysis conducted to measure the sensitivity and specificity of the VSX1 and the HOXA11 methylation biomarkers for diagnosis of bladder cancer.
Figure 4C:
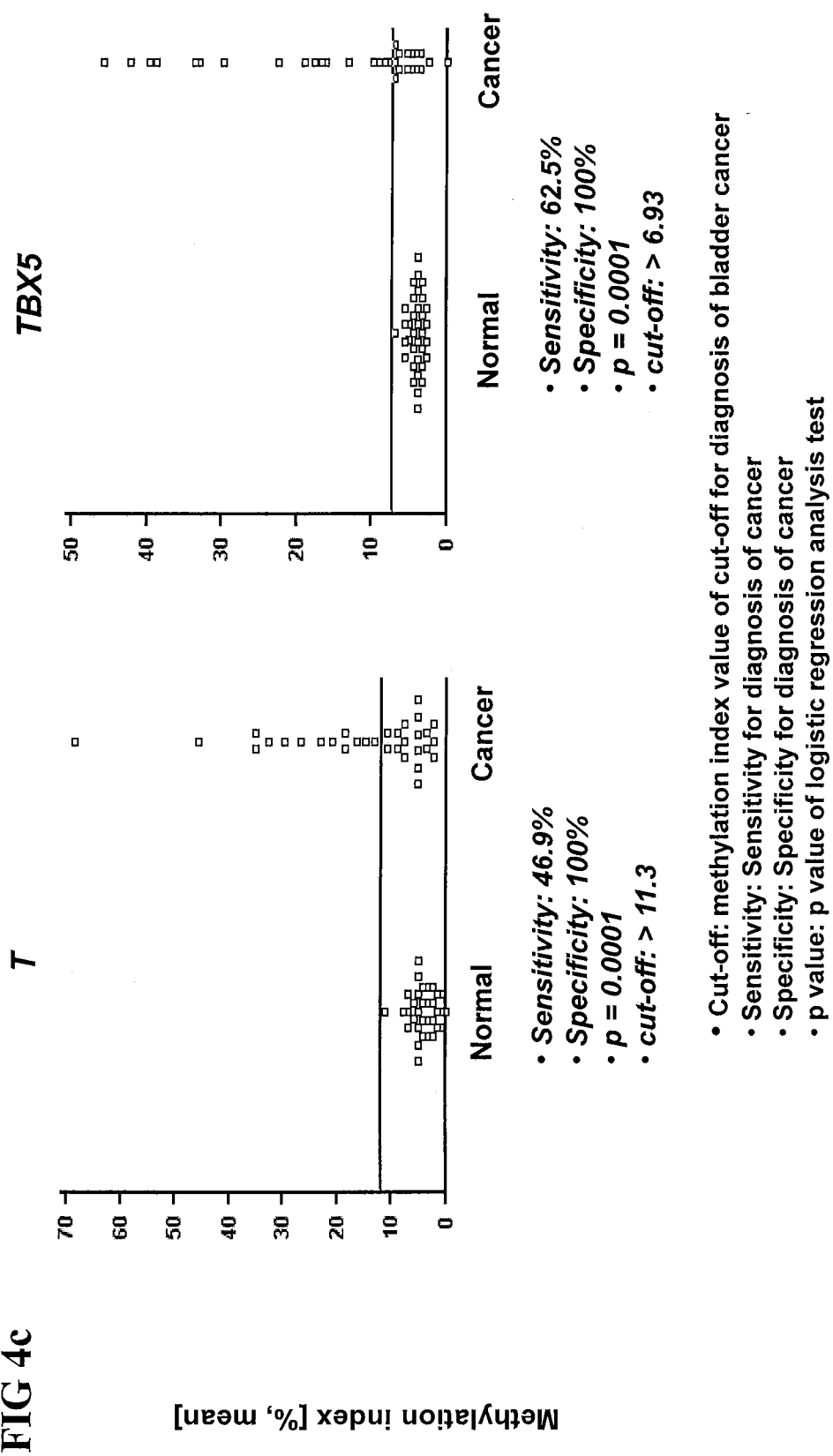
FIG. 4c shows the results of receiver operating characteristic (ROC) curve analysis conducted to measure the sensitivity and specificity of the T and the TBX5 methylation biomarkers for diagnosis of bladder cancer.
Figure 4D:
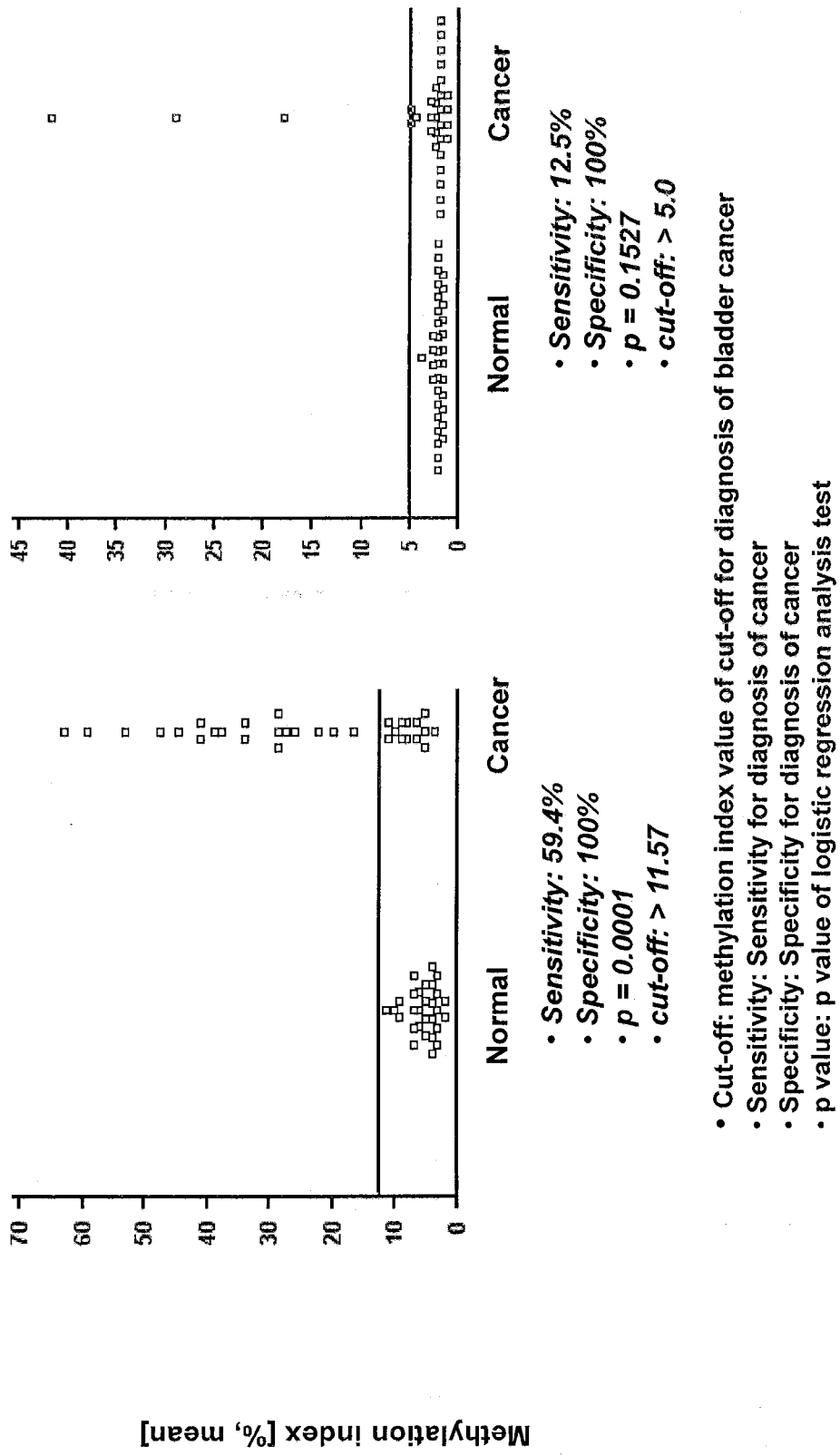
FIG. 4d shows the results of receiver operating characteristic (ROC) curve analysis conducted to measure the sensitivity and specificity of the PENK and the PAQR9 methylation biomarkers for diagnosis of bladder cancer.
Figure 4E:
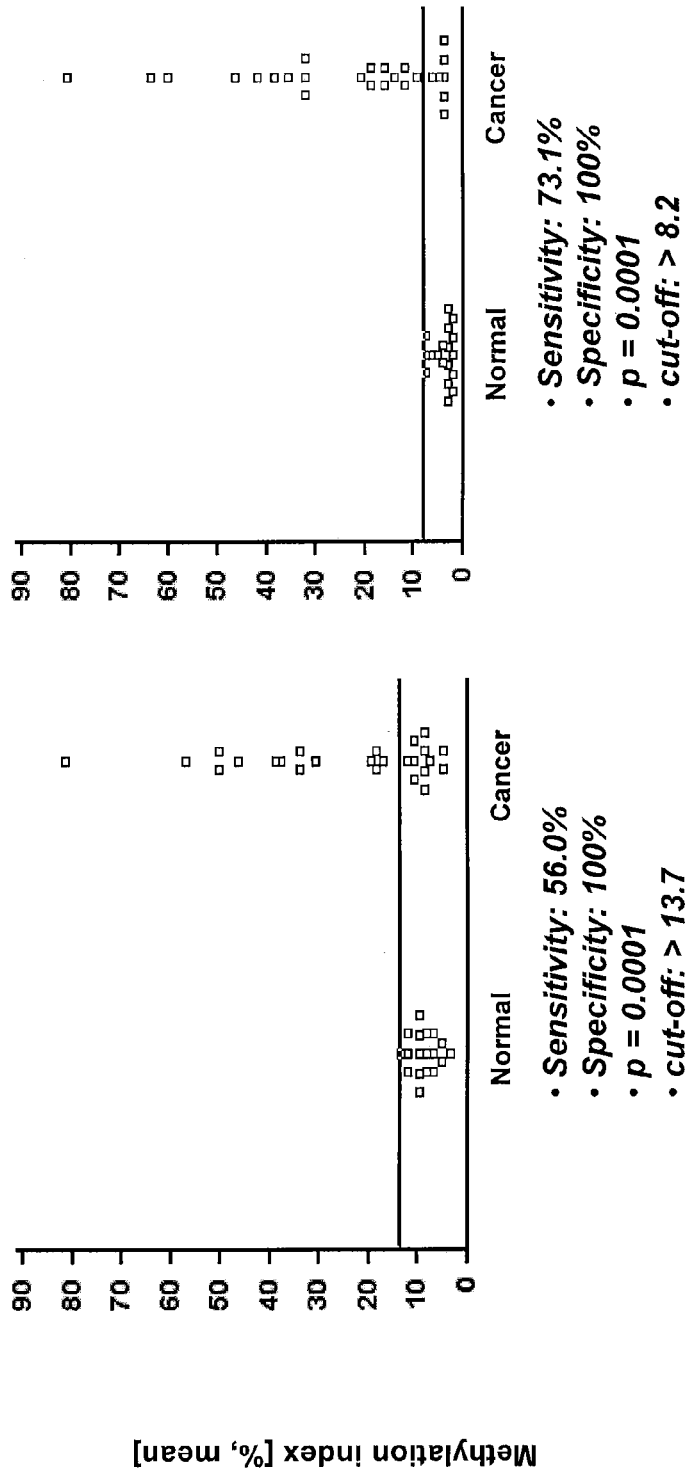
FIG. 4e shows the results of receiver operating characteristic (ROC) curve analysis conducted to measure the sensitivity and specificity of the LHX2 and the SIM2 methylation biomarkers for diagnosis of bladder cancer.

FIG. 2 quantitatively shows the methylation degree of the 10 biomarkers in the bladder cancer cell lines, measured using the pyrosequencing method. As a result, it was shown that the 10 biomarkers were all methylated at high levels in at least one of the cell lines. Table 4 below shows the promoter sequences of the 10 genes.

TABLE 4

Promoter sequences of methylation marker genes

| Gene | SEQ ID NO: |
|---|---|
| CDX2 | 31 |
| CYP1B1 | 32 |
| VSX1 | 33 |
| HOXA11 | 34 |
| T | 35 |
| TBX5 | 36 |
| PENK | 37 |
| PAQR9 | 38 |
| LHX2 | 39 |
| SIM2 | 40 |

Example 3

Measurement of Methylation of Biomarker Genes in Urinary Cells of Bladder Cancer Patients In order to verify whether the 10 genes can be used as biomarkers for diagnosis of bladder cancer, about 20 ml of the urine of each of 20 normal persons and 19 bladder cancer patients was centrifuged in a centrifuge (Hanil Science Industrial Co., Ltd., Korea) at 4,200×g for 10 minutes to isolate cells. The supernatant was discarded, and the cell precipitate was washed twice with 5 ml of PBS. Genomic DNA was isolated from the washed cells using the QJAamp DNA Mini kit (QIAGEN, USA), and 200 ng of the isolated genomic DNA was treated with bisulfite using the EZ DNA methylation-Gold kit (Zymo Research, USA). Then, the DNA was eluted in 20 µl of sterile distilled water and subjected to pyrosequencing.

20 ng of the genomic DNA converted with bisulfite was amplified by PCR. In the PCR amplification, a PCR reaction solution (20 ng of the genomic DNA modified with bisulfite, 5 µl of 10×PCR buffer (Enzynomics, Korea), 5 units of Taq polymerase (Enzynomics, Korea), 4 µl of 2.5 mM dNTP (Solgent, Korea), and 2 µl (10 pmole/µl) of PCR primers) was used, and the PCR reaction was performed in the following conditions: predenaturation at 95° C. for 5 min, and then 45 cycles of denaturation at 95° C. for 40 sec, annealing at 60° C. for 45 sec and extension at 72° C. for 40 sec, followed by final extension at 72 r for 5 min. The amplification of the PCR product was confirmed by electrophoresis on 2.0% agarose gel.

The amplified PCR product was treated with PyroGold reagents (Biotage, USA), and then subjected to pyrosequencing using the PSQ96MA system (Biotage, USA). After the pyrosequencing, the methylation degree of the DNA was measured by calculating the methylation index thereof. The methylation index was calculated by determining the average rate of cytosine binding to each CpG region. After the methylation index of DNA in the urinary cells of the normal persons and the bladder cancer patients has been measured, a methylation index cut-off value for diagnosis of bladder cancer patients was determined through receiver operating characteristic (ROC) curve analysis.

FIGS. 3(A)-3(D) show measurement results for the methylation of the 10 biomarker genes in urinary cells. As can be seen in FIG. 3, the methylation degree of the genes was higher in the sample of the bladder cancer patients than in the sample of the normal persons. Meanwhile, the methylation index in the cystitis patients and the hematuria patients was similar to that in the normal control group or was rarely higher than that in the normal control group. FIGS. 4(a)-4(e) show ROC analysis results for determining cut-off values for diagnosis of bladder cancer. Also, methylation index cut-off values for the 10 biomarkers, calculated based on the ROC curve analysis results, are shown in Table 5 below.

TABLE 5

Cut-off values for bladder cancer diagnosis of 10 biomarkers

| Gene | cut-off (%)[a] |
|---|---|
| CDX2 | 5.82< |
| CYP1B1 | 8.38< |
| VSX1 | 29.3< |
| HOXA11 | 8.81< |
| T | 11.3< |
| TBX5 | 6.93< |
| PENK | 11.57< |
| PAQR9 | 5.0< |
| LHX2 | 13.7< |
| SIM2 | 8.2< |

In the analysis of the methylation of the 10 biomarkers, the methylation index of each biomarker in the clinical sample was calculated. The case in which the calculated methylation index for diagnosis of bladder cancer was higher than the cut-off value obtained through receiver operating characteristic (ROC) analysis was judged to be methylation-positive, and the case in which the calculated methylation index was lower than the cut-off value was judged to be methylation-negative.

Figure 5:
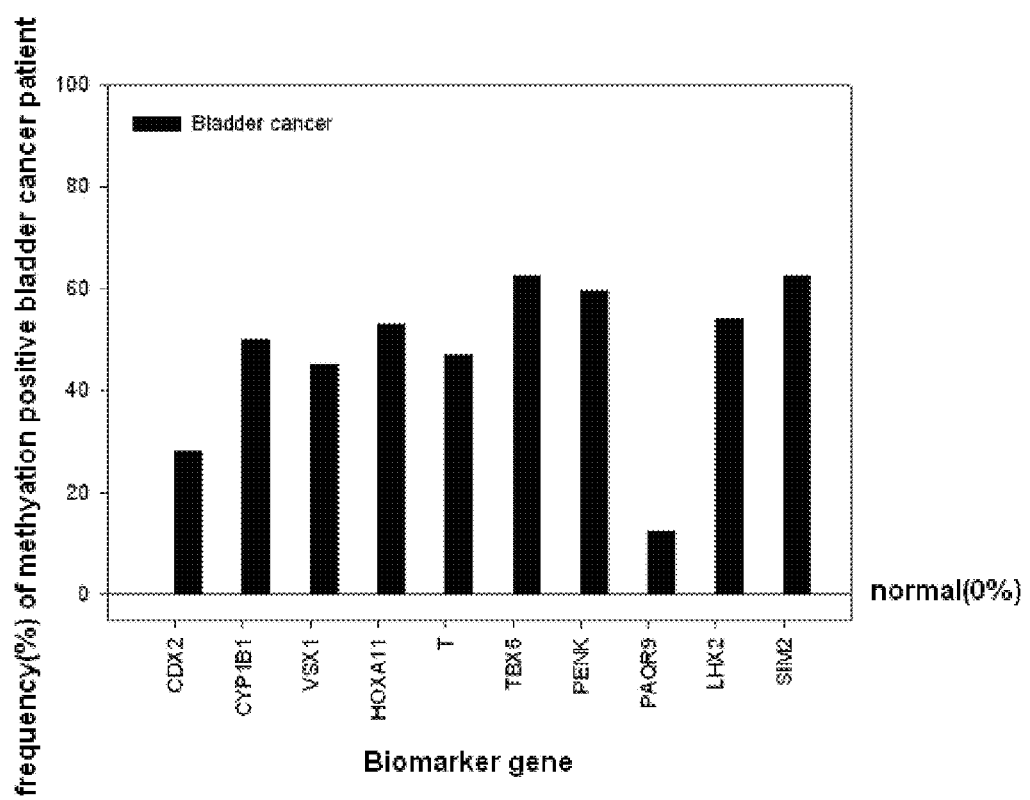
FIG. 5 shows the frequency of methylation in the urinary cells of normal persons and bladder cancer patients.

As shown in Table 6 below and FIG. 5, when judged on the basis of the cut-off value obtained by ROC curve analysis, the urinary cells of the normal persons were methylation-negative for all the 10 biomarkers, but 12.5-62.5% of the samples of the bladder cancer patients were methylation-positive for the 10 biomarkers. Also, statistical analysis was performed and, as a result, it could be seen that 9 of the samples of the bladder cancer samples were methylation-positive for 9 of the 10 biomarkers at a significant level (p<0.01) compared to the normal person group. This suggests that 9 of the 10 methylation markers are statistically significantly methylated specifically in bladder cancer and are highly useful for diagnosing bladder cancer.

TABLE 6

Frequency of methylation-positive samples for 10 biomarkers

| | No. of methylation-positive samples/No. of total samples (%)[a] | | |
|---|---|---|---|
| Gene | Normal | bladder cancer patient | P value[b] |
| CDX2 | 0/31 (0) | 9/32 (28.1) | 0.002 |
| CYP1B1 | 0/31 (0) | 16/32 (50.0) | <0.001 |
| VSX1 | 0/31 (0) | 14/32 (45.2) | <0.001 |
| HOXA11 | 0/31 (0) | 17/32 (53.1) | <0.001 |
| T | 0/31 (0) | 15/32 (46.9) | <0.001 |
| TBX5 | 0/31 (0) | 20/32 (62.5) | <0.001 |
| PENK | 0/31 (0) | 19/32 (59.4) | <0.001 |
| PAQR9 | 0/31 (0) | 4/32 (12.5) | 0.113 |
| LHX2 | 0/17 (0) | 13/24 (54.2) | <0.001 |
| SIM2 | 0/17 (0) | 15/24 (62.5)0 | <0.001 |

[a]frequency of methylation-positive samples; and
[b]p values obtained through the Chi-Square test Example 4

Evaluation of the Ability of 6 Biomarker Panel Genes to Diagnose Bladder Cancer

Figure 6A:
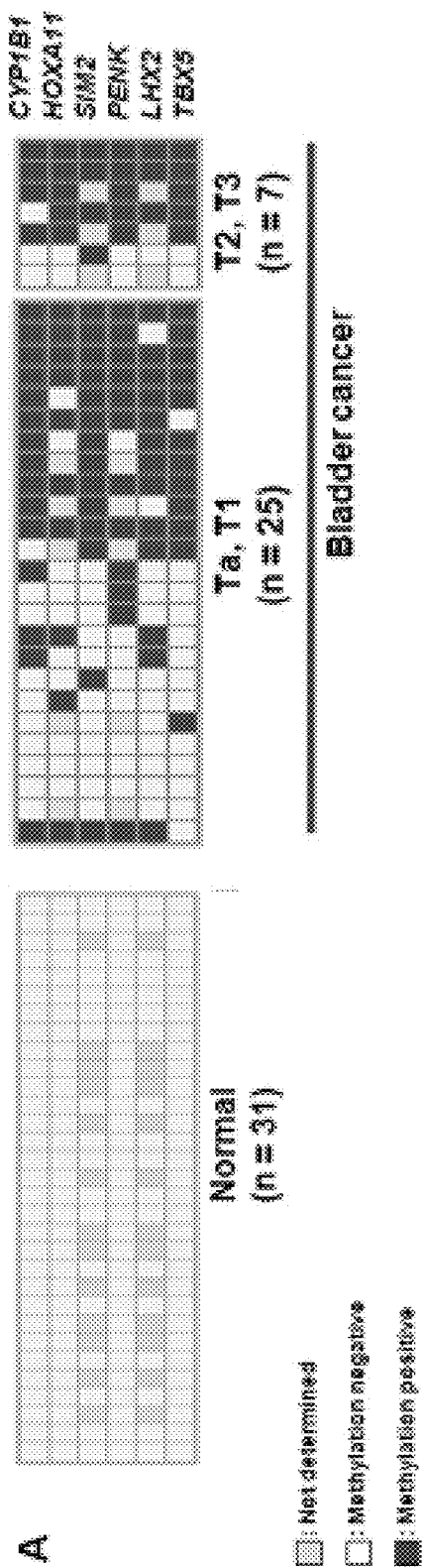
FIGS. 6(A)-6(D) shows the methylation profile of an optimal panel of 6 biomarker genes for bladder cancer diagnosis (FIG. 6(A)), selected from among 10 biomarkers using logistic regression analysis, and shows the sensitivity and specificity of the gene panel for diagnosis of bladder cancer (FIG. 6(B)).
Figure 6B:
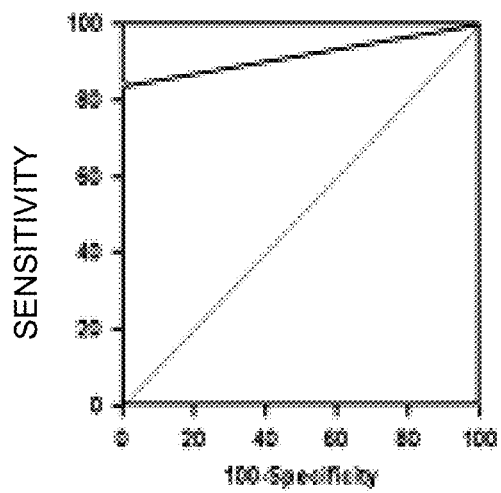
Figure 6C:
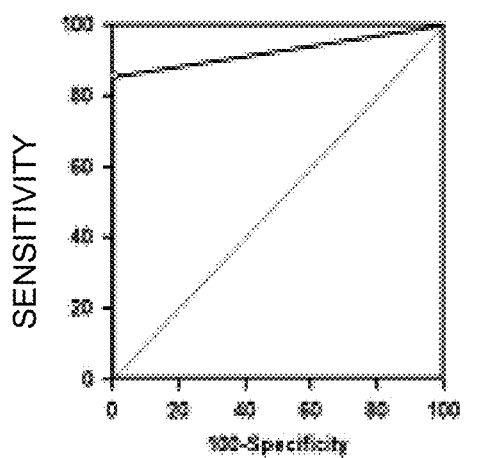
Figure 6D:
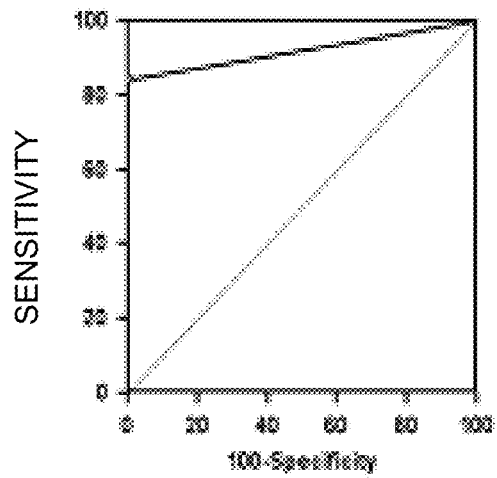

Using the 10 methylation biomarkers, logistic regression analysis was performed. As a result, an optimal panel of 6 genes for diagnosing bladder cancer was established. FIG. 6A shows the methylation status of the 6 biomarkers (CYP1B1, HOXA11, SIM2, PENK, LHX2 and TBX5). Whether samples were methylation-positive or methylation-negative for the 6 genes was judged according to the method described in Example 3. As a result, it could be seen that all the normal samples were methylation-negative for the 6 genes, and only the bladder cancer samples were methylation-positive for the 6 genes. Particularly, early bladder cancer samples were also methylation-positive for the 6 genes at a high frequency, suggesting that the 6 genes are highly useful for early diagnosis of bladder cancer. When the methylation of at least one gene of the gene panel consisting of the six genes was diagnosed as bladder cancer, the sensitivity and specificity of the gene panel for early bladder cancer were as extremely high as 84.0% and 100%, respectively (FIG. 6D). Also, the sensitivity and specificity of the gene panel for advanced bladder cancer were measured to be 85.7% and 100%, respectively (FIG. 6C). In addition, the sensitivity and specificity of the gene panel for all early and advanced bladder cancers were measured to be 84.4% and 100%, respectively (FIG. 6B). This suggests that the methylation of the 6 genes is highly useful for early diagnosis of bladder cancer.

Example 5

Measurement of Methylation of Biomarker Genes Using Methylated DNA-Specific Binding Protein In order to measure the methylation of biomarkers which are methylated specifically in bladder cancer, 100 ng of the genomic DNA of each of the bladder cancer cell lines RT24 and HT1197 was sonicated (Vibra Cell, SONICS), thus obtaining about 200-400-bp genomic DNA fragments.

To obtain only methylated DNA from the genomic DNA, MBD known to bind to methylated DNA was used. Specifically, 2 μg of 6×His-tagged MBD was pre-incubated with 500 ng of the genomic DNA of E. coli JM110 (No. 2638, Biological Resource Center, Korea Research Institute of Bioscience & Biotechnology), and then bound to Ni-NTA magnetic beads (Qiagen, USA). 100 ng of the sonicated genomic DNA was allowed to react with the beads in the presence of binding buffer solution (10 mM Tris-HCl (pH 7.5), 50 mM NaCl, 1 mM EDTA, 1 mM DTT, 3 mM MgCl$_2$, 0.1% Triton-X100, 5% glycerol, 25 mg/ml BSA) at 4° C. for 20 minutes. Then, the beads were washed three times with 500 μl of a binding buffer solution containing 700 mM NaCl, and then methylated DNA bound to the MBD was isolated using the QiaQuick PCR purification kit (QIAGEN, USA).

Then, the DNA methylated DNA bound to the MBD was amplified by PCR using primers of SEQ ID NOS: 41 and 42 corresponding to the promoter region (from −6842 to −6775 bp) of the SIM2 gene.

```
SEQ ID NO: 41:
5'-TTC TTA TTC TCA CCA GAC ATC TCA ACA CCC-3'
```

```
SEQ ID NO: 42:
5'-ATC TCC CAT CCT CCC TCC CAC TCT C-3'
```

The PCR reaction was performed in the following condition: predenaturation at 94° C. for 5 min, and then 40 cycles of denaturation at 94° C. for 30 sec, annealing at 62° C. for 30 sec and extension at 72° C. for 30 sec, followed by final extension at 72° C. for 5 min. The amplification of the PCR product was confirmed by electrophoresis on 2% agarose gel.

Figure 7:
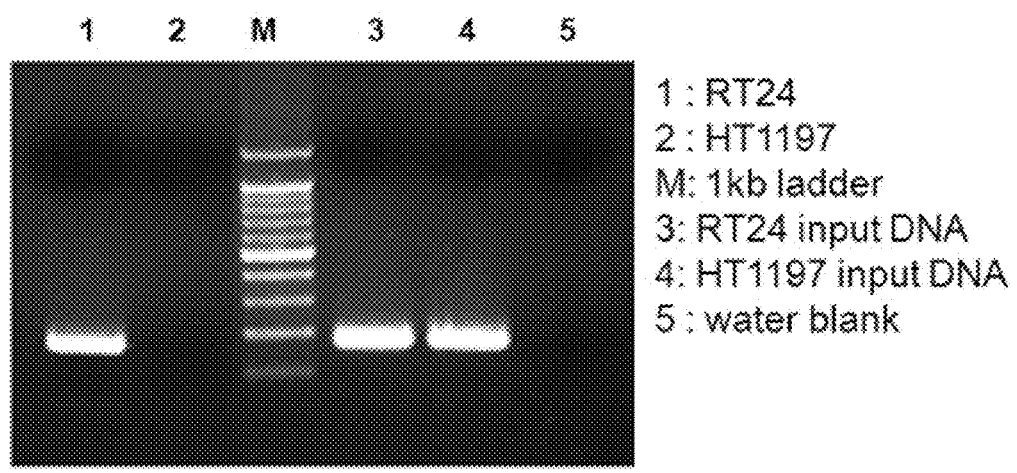
FIG. 7 shows the results of PCR performed using the methylated DNA-specific binding protein MBD in order to measure the methylation of the biomarker SIM2 gene for bladder cancer cell in bladder cancer cell lines.

As a result, it was seen that, for the SIM2 gene, a 168-bp amplified product was detected only in the genomic DNA of the RT24 cell line, suggesting that the gene was methylated, whereas no amplified product was detected in the HT1197 cell line, suggesting that the gene was not methylated in the HT1197 cell line (FIG. 7). Such results were consistent with the methylation measurement results obtained by the pyrosequencing method. Also, such results indicate that the use of MBD enables detection of methylated DNA.

INDUSTRIAL APPLICABILITY

As described above in detail, the present invention provides a kit and nucleic acid chip for diagnosing bladder cancer, which can detect the methylation of CpG islands of bladder cancer-specific marker genes. It is possible to diagnose bladder cancer at an early stage of transformation using the diagnostic kit or nucleic acid chip of the present invention, thus enabling early diagnosis of bladder cancer, and the diagnostic kit or nucleic acid chip can diagnose bladder cancer in a more accurate and rapid manner compared to a conventional method.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

---

What is claimed is:

1. A method for detecting CpG methylation of SIM2-single-minded homolog 2(Drosophila) gene - for bladder carcinoma or bladder cell proliferative disorder diagnosis in a human subject, the method comprising determining hypermethylation of the CpG of the SIM2 gene in genomic DNA isolated from a clinical sample by contacting the sample with primer(s) comprising a DNA sequence selected from the group consisting of SEQ ID NO: 19, 20, 41 and 42 to amplify a methylated CpG of the SIM2 gene, wherein a bladder carcinoma or bladder cell proliferative disorder is detected in the human subject based on increased CpG methylation of the SIM2 gene relative to that of a control.

2. The method according to claim 1, wherein the determination of methylation of the CpG of the SIM2 gene is performed by one selected from the group consisting of PCR, methylation specific PCR, real-time methylation specific PCR, PCR using a methylated DNA-specific binding protein, quantitative PCR, pyrosequencing, and bisulfite sequencing.

3. The method according to claim 1, wherein the clinical sample is tissue, cell, blood, urine, serum or plasma from a patient suspected of cancer or a subject to be diagnosed.

4. The method according to claim 1, wherein the determination of methylation of the CpG of the SIM2 gene comprises examining a CpG methylation of a promoter region of SIM2 in the clinical sample.

5. The method according to claim 4, wherein the promoter comprises a DNA sequence represented in SEQ ID NO: 40.

6. The method according to claim 1, wherein the method further comprises the step of examining CpG methylation of a gene selected from the group consisting of TBX5-T-box 5; CDX2-caudal type homeobox transcription factor 2; CYP1B1- cytochrome P450, family 1, subfamily B, polypeptide 1; VSX-visual system homeobox 1 homolog, CHX10-like (zebrafish); HOXA11-homeobox A11; T-T, brachyury homolog (mouse); PENK- proenkephalin; PAQR9-progestin and adipoQ receptor family member IV; and LHX2- LIM Homeobox 2.

7. The method according to claim 6, wherein the step of examining comprises examining CpG methylation of a promoter or exon region of the gene selected from the group consisting of TBX5; CDX2; CYP1B1; VSX1; HOXA11; T; PENK; PAQR9; and LHX2.

* * * * *